United States Patent
Zhao et al.

(10) Patent No.: US 9,387,332 B2
(45) Date of Patent: Jul. 12, 2016

(54) IMPLANTABLE MEDICAL DEVICES HAVING HOLLOW SLEEVE COFIRE CERAMIC STRUCTURES AND METHODS OF FABRICATING THE SAME

(71) Applicant: MEDTRONIC, INC., Minneapolis, MN (US)

(72) Inventors: Yanzhu Zhao, Blaine, MN (US); Nicholas C. Wine, Minneapolis, MN (US); Joyce K. Yamamoto, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 328 days.

(21) Appl. No.: 14/062,933

(22) Filed: Oct. 25, 2013

(65) Prior Publication Data

US 2015/0097734 A1    Apr. 9, 2015

Related U.S. Application Data

(60) Provisional application No. 61/888,075, filed on Oct. 8, 2013.

(51) Int. Cl.

| | |
|---|---|
| *A61N 1/372* | (2006.01) |
| *A61B 5/00* | (2006.01) |
| *H01Q 1/12* | (2006.01) |
| *H01Q 1/27* | (2006.01) |
| *H01Q 1/36* | (2006.01) |
| *H01Q 11/08* | (2006.01) |
| *H01Q 23/00* | (2006.01) |
| *A61N 1/375* | (2006.01) |
| *A61N 1/362* | (2006.01) |
| *A61B 5/042* | (2006.01) |

(52) U.S. Cl.
CPC .......... *A61N 1/37229* (2013.01); *A61B 5/0022* (2013.01); *A61N 1/362* (2013.01); *A61N 1/3756* (2013.01); *H01Q 1/12* (2013.01); *H01Q 1/27* (2013.01); *H01Q 1/273* (2013.01); *H01Q 1/362* (2013.01); *H01Q 11/08* (2013.01); *H01Q 23/00* (2013.01); *A61B 5/042* (2013.01); *A61B 2560/04* (2013.01); *Y10T 29/49018* (2015.01)

(58) Field of Classification Search
None
See application file for complete search history.

(56) References Cited

U.S. PATENT DOCUMENTS

| | | |
|---|---|---|
| 5,470,345 A | 11/1995 | Hassler et al. |
| 5,951,594 A | 9/1999 | Kerver |
| 6,009,350 A | 12/1999 | Renken |
| 6,693,604 B2 | 2/2004 | Washiro et al. |
| 6,708,065 B2 | 3/2004 | Von Arx et al. |
| 6,788,254 B2 | 9/2004 | Oh et al. |
| 6,931,284 B2 | 8/2005 | Engmark et al. |

(Continued)

FOREIGN PATENT DOCUMENTS

| | | |
|---|---|---|
| WO | 2006131302 | 12/2006 |
| WO | 2007035443 | 3/2007 |

(Continued)

*Primary Examiner* — Brian T Gedeon
(74) *Attorney, Agent, or Firm* — Michael J. Ostrom

(57) ABSTRACT

An implantable medical device (IMD) antenna and methods of fabricating the same are provided. An IMD can include a ceramic structure having at least one wall defining a hollow cavity. The ceramic structure can include a first end and a second end distal from the first end, the first and second ends being open to provide access to the hollow cavity. The IMD also includes an antenna cofire-integrated into the at least one wall of the ceramic structure and a housing adjoined to the ceramic structure.

21 Claims, 35 Drawing Sheets

(56) References Cited

U.S. PATENT DOCUMENTS

| | | |
|---|---|---|
| 6,963,309 B2 | 11/2005 | Andersson et al. |
| 7,047,076 B1 | 5/2006 | Li et al. |
| 7,068,491 B1 | 6/2006 | Burdon et al. |
| 7,164,572 B1 | 1/2007 | Burdon et al. |
| 7,307,597 B2 | 12/2007 | Okayama |
| 7,317,946 B2 | 1/2008 | Twetan et al. |
| 7,554,493 B1 | 6/2009 | Rahman |
| 7,650,191 B1 | 1/2010 | Lim et al. |
| 8,620,449 B2 | 12/2013 | Zhao et al. |
| 2002/0166618 A1 | 11/2002 | Wolf et al. |
| 2006/0092079 A1 | 5/2006 | de Rochemont |
| 2006/0247539 A1 | 11/2006 | Schugt et al. |
| 2007/0060969 A1 | 3/2007 | Burdon et al. |
| 2007/0060970 A1 | 3/2007 | Burdon et al. |
| 2007/0100385 A1 | 5/2007 | Rawat et al. |
| 2007/0123949 A1 | 5/2007 | Dabney et al. |
| 2007/0236861 A1 | 10/2007 | Burdon et al. |
| 2009/0228074 A1 | 9/2009 | Edgell et al. |
| 2009/0228076 A1 | 9/2009 | Ameri |
| 2010/0109958 A1 | 5/2010 | Haubrich et al. |
| 2010/0109966 A1 | 5/2010 | Mateychuk et al. |
| 2010/0114245 A1 | 5/2010 | Yamamoto et al. |
| 2010/0114246 A1 | 5/2010 | Yamamoto et al. |
| 2010/0168817 A1 | 7/2010 | Yamamoto et al. |
| 2010/0168818 A1 | 7/2010 | Barror et al. |
| 2010/0284124 A1 | 11/2010 | Iyer |
| 2011/0029036 A1 | 2/2011 | Yamamoto et al. |
| 2011/0048770 A1 | 3/2011 | Reiterer et al. |
| 2011/0102967 A1 | 5/2011 | Munns et al. |
| 2011/0106205 A1 | 5/2011 | Reiterer et al. |
| 2011/0106228 A1 | 5/2011 | Reiterer et al. |
| 2011/0125210 A1 | 5/2011 | Francis et al. |
| 2012/0001812 A1 | 1/2012 | Zhao et al. |
| 2012/0081201 A1 | 4/2012 | Norgaard et al. |
| 2012/0307416 A1 | 12/2012 | Iyer |
| 2013/0032378 A1 | 2/2013 | Morioka et al. |
| 2013/0032391 A1 | 2/2013 | Morioka et al. |
| 2013/0032392 A1 | 2/2013 | Morioka et al. |
| 2013/0058003 A1 | 3/2013 | Iyer et al. |
| 2013/0138186 A1 | 5/2013 | Iyer et al. |

FOREIGN PATENT DOCUMENTS

| | | |
|---|---|---|
| WO | 2008032746 A1 | 3/2008 |
| WO | 2010051230 | 5/2010 |
| WO | 2010077897 | 7/2010 |
| WO | 2010078100 | 7/2010 |
| WO | 2011037648 | 3/2011 |

IMPLANTABLE MEDICAL DEVICES HAVING HOLLOW SLEEVE COFIRE CERAMIC STRUCTURES AND METHODS OF FABRICATING THE SAME

This application claims the benefit of U.S. Provisional Application No. 61/888,075, filed on Oct. 8, 2013, the content of which is incorporated herein by reference in its entirety.

TECHNICAL FIELD

The subject disclosure relates generally to an implantable medical device (IMD) and, more particularly, to an IMD having a cofire ceramic structure (CCS).

BACKGROUND

IMDs regularly provide functions for physiological health that are of critical importance in maintaining life as well as quality of life. For example, implantable pacemakers can deliver electrical pulses to the heart of the wearer of the IMD to maintain the heart beat at a normal rate. As another example, an implantable defibrillator can deliver electrical energy to the heart of the wearer of the IMD upon detection of ventricular fibrillation, cardiac dysrhythmia or pulseless ventricular tachycardia to increase likelihood of the heart returning to a normal sinus rhythm. As another example, an implantable neurostimulator can deliver electrical energy to the nervous system to reduce pain of the wearer of the IMD. As another example, an implantable deep brain stimulation device can deliver electrical energy to the brain upon detection of symptoms of neurological movement disorders to increase likelihood of return to greater physiological muscle control.

Medical care providers can monitor the IMD and assess patient current and historical physiological state to monitor the patient's condition. Providers can also initiate and modify treatment plans from time to time and/or evaluate patient compliance with nutrition, exercise and general care regiments based on data recorded in the IMD. Additionally, personnel can perform IMD diagnostics to improve function efficiencies and detection of low remaining battery life or other device or lead conditions.

Typically, patients visit a medical facility for IMD monitoring and/or retrieval of data from an IMD. Monitoring and testing of IMD data and/or modification of parameters for IMD functionality can also be facilitated remotely using one or more computer networks. For example, patient-related data can be retrieved wirelessly in some cases. In any case, the communication of information to and from the device is typically facilitated via telemetry.

Advances in technology (e.g., materials processes and integrated circuit technology) have facilitated an onslaught of the development of IMDs. However, while antennas can facilitate wireless telemetry, and thereby improve patient convenience and compliance, antenna design for IMDs presents numerous difficulties. Size and packaging constraints are particularly stringent and challenging. As such, systems, methods and apparatus associated with IMDs that employ CCSs suited to telemetry functions are desired.

SUMMARY

The following presents a simplified summary of one or more of the embodiments in order to provide a basic understanding of various aspects described herein. This summary is not an extensive overview of the embodiments described herein. It is intended to neither identify key or critical elements of the embodiments nor delineate any scope of embodiments or the claims. Its sole purpose is to present some concepts of the embodiments in a simplified form as a prelude to the more detailed description that is presented later. It will also be appreciated that the detailed description can include additional or alternative embodiments beyond those described in the Summary section.

Embodiments described herein include IMDs, and methods of fabricating IMDs. In some embodiments, the IMD includes a ceramic structure having at least one wall defining a hollow cavity, wherein the ceramic structure includes a first end and a second end distal from the first end, the first and second ends being open to provide access to the hollow cavity, an antenna cofire-integrated into the at least one wall of the ceramic structure, and a housing adjoined to the ceramic structure. The antenna can be a three-dimensional antenna having any number of different configurations including, but not limited to, substantially serpentine-shaped or substantially helical-shaped, antenna configurations.

In some embodiments, a component (e.g., passive network component or integrated circuit) is located within the hollow cavity of the ceramic structure. By way of example, but not limitation, the component can include an element of an impedance matching network such as a capacitor or inductor, a passive filter, a resistor, a transistor, a tunnel diode, and/or any other component that performs one or more electrical functions and is not an antenna.

In some embodiments, the IMD can also include a cofire-integrated metal pad in or on an exterior surface of the ceramic structure. The cofire-integrated metal pad can be configured to provide conductivity between the cofire-integrated antenna and one or more components in the housing of the IMD.

In some embodiments, a method of fabricating an IMD includes providing a plurality of layers of dielectric material, and forming a hollow cavity in the plurality of layers of dielectric material. The method can also include depositing material of which an antenna is composed on at least one of the plurality of layers. The method can also include forming a ceramic structure having a cavity extending through the ceramic structure and comprising a cofire-integrated antenna in a wall of the ceramic structure based, at least, on cofiring the plurality of layers of dielectric material and the material of which the antenna is composed.

Toward the accomplishment of the foregoing and related ends, the one or more embodiments can include the aspects hereinafter described and particularly pointed out. The following description, claims and annexed drawings set forth herein detail certain illustrative aspects of one or more of the embodiments. These aspects are indicative, however, of but a few of the various ways in which the principles of various embodiments can be employed, and the described embodiments are intended to include all such aspects and their equivalents.

DETAILED DESCRIPTION

Figure 1:
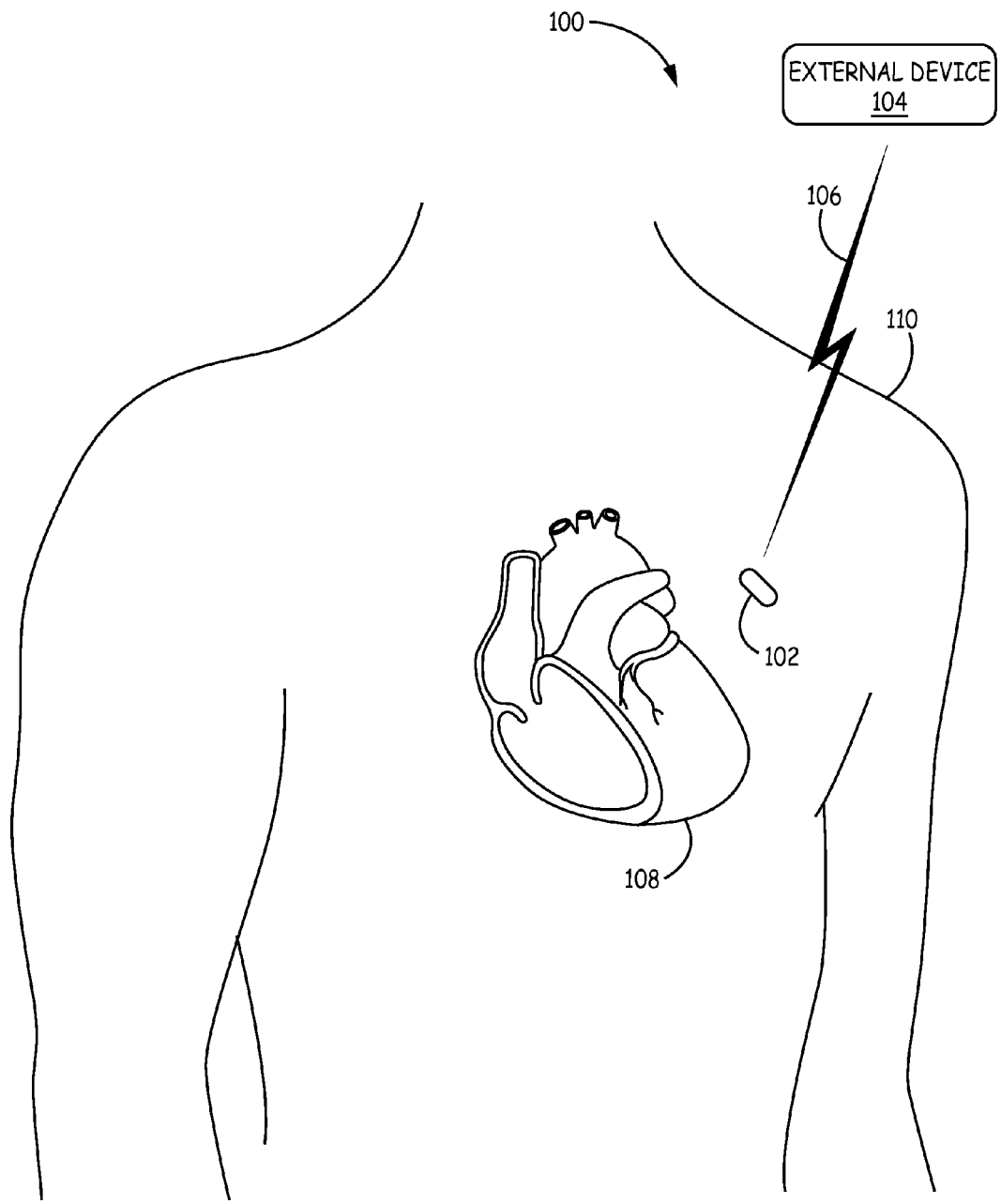
FIG. 1 illustrates a schematic diagram of an exemplary non-limiting medical device telemetry system including an external device and an IMD with CCS having cofire-integrated antenna in accordance with one or more embodiments described herein.

The following detailed description is merely illustrative and is not intended to limit embodiments or application and uses of embodiments. Furthermore, there is no intention to be bound by any expressed or implied theory presented in the preceding Technical Field, Background or Summary sections, or in the following Detailed Description section.

One or more embodiments are now described with reference to the drawings, wherein like reference numerals are used to refer to like elements throughout. In the following description, for purposes of explanation, numerous specific details are set forth in order to provide a more thorough understanding of the various embodiments. It is evident, however, that the various embodiments can be practiced without these specific details.

Additionally, the following description refers to components being "connected," "coupled," "attached" and/or "adjoined" to one another. As used herein, unless expressly stated otherwise, the terms "connected," "coupled," "attached" and/or "adjoined" mean that one component is directly or indirectly connected to another component, mechanically, electrically or otherwise (e.g., via seal). Thus, although the figures may depict example arrangements of components, additional and/or intervening components may be present in one or more embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word "example" or "exemplary" is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application should generally be construed to mean "one or more" unless specified otherwise or clear from context to be directed to a singular form. The terms "first," "second," "third," and so forth, as used in the claims and description, unless otherwise clear by context, is for clarity only and doesn't necessarily indicate or imply any order in time.

An overview of the embodiments follows. Apparatus, systems and/or methods described herein relate to IMDs having CCSs with cavities and cofire-integrated antennas. The cofire-integrated antennas can be any number of different configurations including, but not limited to, substantially serpentine-shaped, substantially helical-shaped, meandering and/or substantially fractal-shaped, antenna configurations.

In various embodiments, one or more different components can be cofire-integrated into the wall of the CCS or provided in the cavity of the CCS. The components can be any number of different components that can perform one or more electrical functions and/or output one or more electrical signals. By way of example, but not limitation, the component can be a feedthrough, sensing electrode, integrated circuit, passive network (or component thereof) or the like.

In various embodiments, the CCS can be designed with biocompatible and biostable materials and can therefore directly contact bodily fluids in these embodiments. By contrast, the CCS can be designed with non-biocompatible and non-biostable materials and, in these embodiments, can be disposed in a hermetically sealed housing to reduce the likelihood of contact with bodily fluids and gases.

The CCS can include one or more interconnections between different layers or regions of the CCS. In some instances, conductive pads or plates can be arranged on different layers to provide a capacitive interconnection between the various layers or regions of the CCS. Alternatively, traditional conductive via interconnections can be employed to provide conductivity between the layers of the CCSs.

In some embodiments, a metal pad is cofire-integrated into an external surface of the CCS and can be conductively coupled between the antenna of the CCS and one or more components of the IMD. In some embodiments, a feedthrough is cofire-integrated into the CCS and can be conductively coupled between the antenna of the CCS and one or more components of the IMD. As used herein, the term "feedthrough" means a conductive structure configured to conductively couple one component (e.g., antenna, radio frequency (RF) device) to one or more other components. In some embodiments, the feedthrough can include a feedthrough conductivity portion adapted to facilitate conductivity. The feedthrough conductivity portion can be surrounded by insulative material. The feedthrough can provide an electrically conductive path from the antenna of the CCS to the component in the housing of the IMD, for example.

The CCS can be encapsulated in a polymer housing, which can optionally also be a device header in some embodiments. For example, the device header can include components or electrical conduits electrically coupleable within the IMD.

Embodiments described herein can employ cofire ceramic technology to generate CCSs that facilitate telemetry to/from IMDs. The use of ceramic materials can enable fabrication of substantially RF transparent, mechanically rigid structures having small size profiles desired for implantable devices. These substantially RF transparent structures can facilitate communication of RF signals through the structures without substantial shielding or signal attenuation. This thereby improves efficiency of the antenna, which may reduce the power consumption utilized for communication, which in turn may increase the longevity of the IMD.

Further, one or more embodiments disclosed herein can advantageously increase efficiency of an IMD through utilization of the hollow cavity for components. The hollow cavity can provide low dielectric properties because the lower dielectric constant of the cavity provides improved isolation of the electrical circuit placed inside the cavity, reducing coupling to the antenna and thus minimally impacting the antenna performance. This attribute enables closer separation distances between the antenna and associated electrical circuitry and higher system packaging density and miniaturization. Moreover, placement of components within the hollow cavity of the ceramic structure can further reduce the size of the IMD since the number of components within the housing of the IMD can be reduced.

Finally, embodiments having capacitive interconnections can provide for a reduced CCS wall thickness (and facilitate corresponding reduced antenna volume) relative to embodiments having through hole via interconnections.

Turning now to the figures, FIG. 1 illustrates a schematic diagram of an exemplary non-limiting medical device telemetry system 100. Medical device telemetry system 100 includes IMD 102 and external device 104 communicatively coupleable to IMD 102 via wireless channel 106.

IMD 102 can perform any number of functions for detection and/or treatment of medical conditions. For example, in one embodiment, IMD 102 can be a subcutaneous sensing device configured to sense signals indicative of one or more physiological parameters of human body 110. IMD 102 can be an insertable cardiac monitor configured to sense and/or store electrocardiogram (ECG) signals. In some examples, IMD 102 can be configured to sense ECG or other signals and detect arrhythmias, e.g., ventricular and/or supra-ventricular arrhythmias, based on the signals. In other instances, IMD 102 can alternatively or additionally be configured to deliver therapy to human body 110.

FIG. 1 further depicts external device 104 in communication with IMD 102 via wireless channel 106. In some examples, external device 104 comprises a handheld computing device, programmer, computer workstation, or networked computing device. External device 104 can include a user interface that presents information to and facilitates receipt of input from a user (e.g., physician). It should be noted that the user can also interact with external device 104 remotely via a networked computing device.

A user, such as a physician, technician, surgeon, electrophysiologist, other clinician, nurse, or patient, interacts with external device 104 to communicate with IMD 102. For example, the user can interact with external device 104 to retrieve physiological or diagnostic information from IMD 102. A user can also interact with external device 104 to program IMD 102, e.g., select values for operational parameters of the IMD 102. For example, the user can use external device 104 to retrieve information from IMD 102 regarding the rhythm of heart 108, trends therein over time, or arrhythmic episodes.

IMD 102 and external device 104 can communicate via wireless communication using various techniques known in the art. Examples of communication techniques can include, for example, low frequency or RF telemetry, proximal inductive telemetry (e.g., via magnetic field coupling), or tissue conductance communication, but other techniques are also contemplated. In some examples, external device 104 can include a programming head that can be placed proximate to or in contact with the patient's body near an implant site for IMD 102 to improve quality or security of communication between IMD 102 and external device 104.

External device 104 can be or include any type of device configured to process, store, display, analyze and/or test medical device telemetry data. For example, external device 104 can include, but is not limited to, a personal computer, laptop, smart phone or the like. In various embodiments, external device 104 can include programs, modules, hardware, software and/or computer-readable storage media to facilitate monitoring, testing, analyzing, processing, storage and/or display of data associated with information retrieved from IMD 102. In various embodiments, one or more of external device 104 can include, or be communicatively coupled to, a receiver (not shown) configured to receive signals from an antenna of IMD 102. External device 104 can be communicatively coupled to a transmitter and antenna configured to transmit information to the antenna of IMD 102.

In some embodiments, external device 104 can transmit information to IMD 102 to update operation of IMD 102. By way of example, but not limitation, external device 104 can transmit information to cause an update in parameter values to change operation of IMD 102. In particular, the information transmitted from external device 104 to IMD 102 and/or a processor of IMD 102 can cause a modification in operation of IMD 102.

As will be described in further detail herein, IMD 102 includes a CCS that includes a cofire-integrated antenna in accordance with one or more embodiments described herein. The CCS can, in various instances, be a header of IMD 102 or a sleeve of IMD 102. The header or sleeve can be formed separately from the remainder of the housing of IMD 102 and attached during assembly of IMD 102. As such, in some instances, the CCS may form a portion of the housing of IMD 102 (e.g., be exposed to the body of patient 110) to enclose and hermetically seal in the components of IMD 102. Further, in some embodiments, a second housing can encapsulate the CCS or the portion of the CCA exposed to human body 110. In this case, CCS does not form a portion of the housing of IMD 102 that is exposed to the body of patient 110. For example, CCS may be a component that is integrated within a header of a device, but not function as the header.

Figure 2:
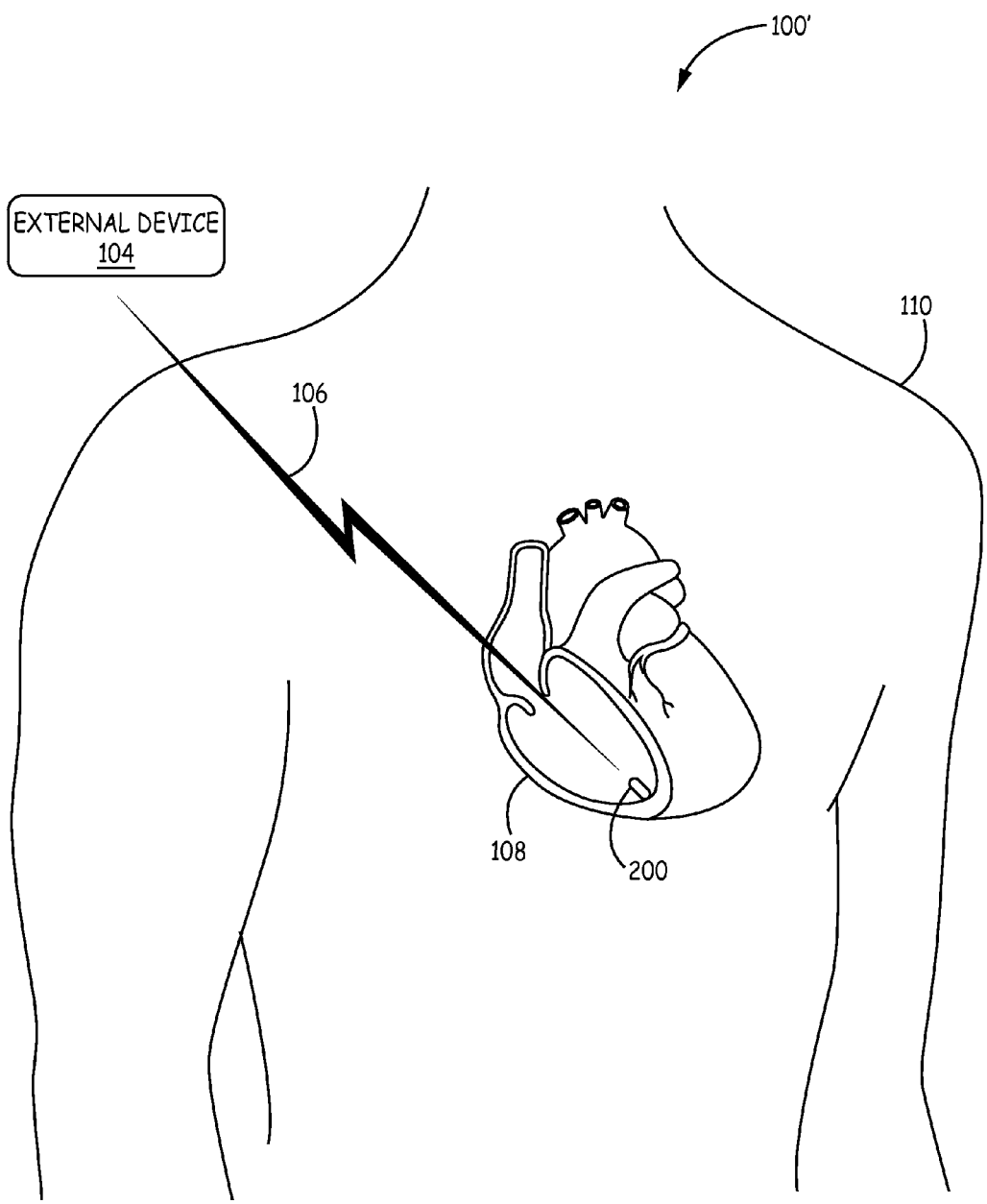
FIG. 2 illustrates a schematic diagram of an exemplary non-limiting medical device telemetry system including an external device and an IMD with CCS having cofire-integrated antenna in accordance with one or more embodiments described herein.

FIG. 2 is a schematic diagram illustrating an exemplary medical device telemetry system 100'. In various embodiments, system 100' can include one or more of the structure and/or functionality of system 100 (and vice versa). Repetitive description of like elements employed in other embodiments is omitted for sake of brevity.

Medical device telemetry system 100' conforms substantially to system 100 of FIG. 1 in structure and/or function, except IMD 200 is or includes an implantable leadless IMD (e.g., implantable leadless pacemaker) implanted within a ventricle of heart 108 of human body 110. IMD 200 includes one or more electrodes (not illustrated in FIG. 2) via which IMD 200 provides electrical stimulation to the ventricle of heart 108 of human body 110, such as one or more pacing pulses. Additionally or alternatively, IMD 200 can sense electrical signals attendant to the depolarization and repolarization of the heart 108 via the one or more electrodes. In one example, IMD 200 provides therapy to human body 110 based on sensed physiological signals.

Although IMD 102 of FIG. 1 is illustrated as being implanted subcutaneously in a left pectoral region of human body 110 and IMD 200 of FIG. 2 is illustrated as being implanted within a left ventricle of heart 108, IMD 102 and/or IMD 200 can be implanted in other locations. For example, IMD 200 can be positioned within any suitable region of human body 110, such as within an atrium of heart 108 or at an epicardial location of heart 108. In some examples, depending on the location of implant, IMD 200 can include other sensing and/or stimulation functionalities. In some examples, system 100' can include a plurality of leadless IMDs 200, e.g., to provide stimulation and/or sensing at a variety of locations.

Although the examples described herein generally refer to a leadless IMD, in some embodiments, IMD 102 and/or IMD 200 can alternatively be coupled to one or more leads including one or more electrodes configured to sense the one or more physiological parameters of human body 110 and/or to deliver therapy to heart 108 of human body 110. Moreover, although described generally as cardiac IMDs, the CCSs described herein may be used within other implantable devices including, but not limited to neurological devices, drug pumps, or other implantable devices.

Moreover, although the examples described in FIGS. 1 and 2 illustrate a medical device telemetry system that includes an IMD and an external device, the IMDs of FIGS. 1 and 2 may communicate with any devices, including other implanted devices, body-worn devices, and other external devices.

Figure 3:
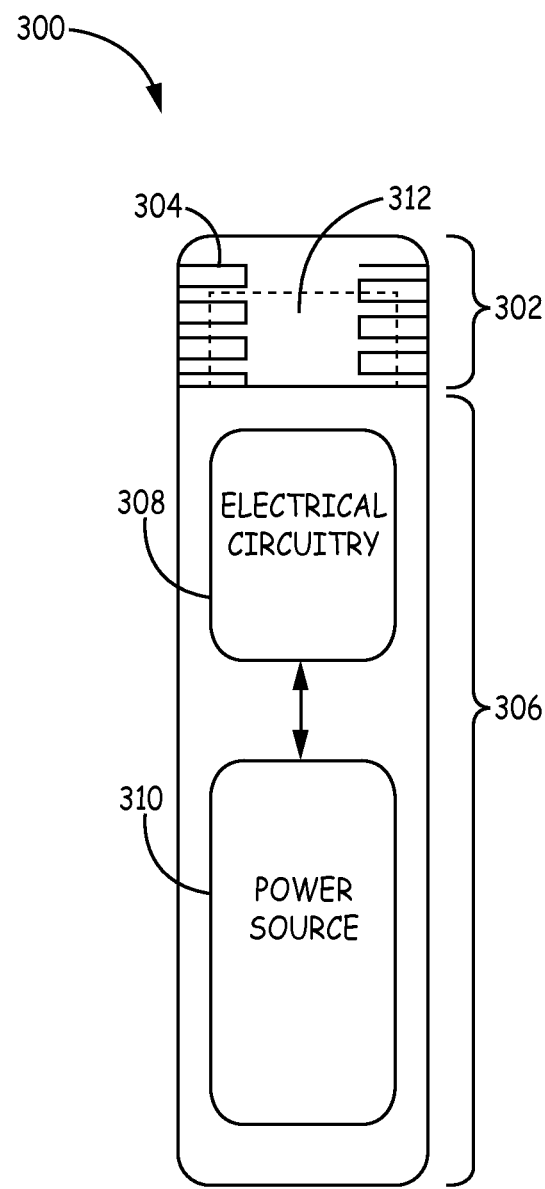
FIG. 3 illustrates a cross-sectional view of an exemplary non-limiting IMD having a CCS in accordance with embodiments described herein.

FIG. 3 illustrates a cross-sectional view of an exemplary non-limiting IMD 300 having a CCS 302 in accordance with embodiments described herein. In various embodiments, IMD 300 can include one or more of the structure and/or functionality of IMD 102, 200 (and vice versa). Repetitive description of like elements employed in other embodiments is omitted for sake of brevity.

As shown, IMD 300 can include housing 306 and CCS 302 having a cofire-integrated antenna 304 embedded in CCS 302. In some embodiments, antenna 304 can be completely encapsulated within the walls of CCS 302. IMD 300 can also include electrical circuitry 308 and/or power source 310 configured to power IMD 300 and located in housing 306. In various embodiments, one or more of CCS 302 having cofire-integrated antenna 304 embedded in CCS 302, housing 306, electrical circuitry 308 and/or power source 310 can be communicatively and/or electrically coupled to one another to perform one or more functions of IMD 300.

Antenna 304 can be configured to transmit and/or receive information to and/or from external device 104, which is illustrated in FIGS. 1 and 2. By way of example, but not limitation, antenna 304 can transmit signals including information indicative of a biological event of human body 110, current and/or historical data generated by IMD 300, remaining battery life of IMD 300 and/or diagnostic information associated with functionality and/or operation of IMD 300. By way of other examples, but not limitation, antenna 304 can receive signals from external device 104 that include information indicative of one or more parameter values by which IMD 300 operates. The information can be received at IMD 300 and/or electrical circuitry 308 of IMD 300 and cause IMD 300 to modify parameter values by which IMD 300 operates.

In various embodiments, antenna 304 can transmit and/or receive signals including information indicative of past or current activity (e.g., heart rhythms, heart rate, arterial blood oxygen saturation, cardiac output, intravascular pressures, blood pressure, blood temperature, blood oxygen level, heart electrical activity, brain electrical activity, level of quinolinic acid, neurotransmitters, nerve activity, nerve-muscle activity or spinal cord nerve activity). In some embodiments, antenna 304 can transmit and/or receive signals including information indicative of past or current events (e.g., heart attacks, heart failure, arrhythmias, unrecognized myocardial infarctions, chronic pain nerve signals, brain aneurysms, neurological injury, stroke, brain injury).

In some embodiments, antenna 304 can transmit and/or receive signals having information to cause IMD 300 to perform any number of functions including, but not limited to, outputting electrical signals (e.g., stimulation) to one or more organs, muscles, nervous system and/or spinal cord in human body 110, brain stimulation, interruption of pain signals, spinal cord stimulation, monitoring and/or sensing activity of one or more organs in human body 110 and/or monitoring and/or identification of defined chemicals (or levels of defined chemicals) in human body 110.

Antenna 304 can be formed from conductive material deposited on a plurality of dielectric layers. In various embodiments, numerous interconnects (not shown in FIG. 3) can be provided in a pattern corresponding to desired configuration of antenna 304 such that conductivity for antenna 304 can be provided between the plurality of dielectric layers of CCS 302. While the embodiment illustrated in FIG. 3 is a cross-sectional view, as described herein, antenna 304 is a three-dimensional antenna. As such, the configuration of antenna 304 can be a three-dimensional configuration across numerous regions within CCS 302. Other configurations for three-dimensional antennas can also be cofire-integrated into CCS 302 in other embodiments. By way of example, but not limitation, the cofire-integrated antenna can have one or more portions that are substantially helical-shaped, meandering, substantially spiral-shaped or substantially fractal-shaped configuration. In various embodiments, antenna 304 can be designed to have different radiation patterns, materials and/or parameters to facilitate radiation of electromagnetic energy with different devices and/or in different environments.

Further, while the embodiment illustrated in FIG. 3 includes only one three-dimensional antenna, in other embodiments, more than one three-dimensional antenna can be integrated into a single CCS via the cofiring process. For example, two concentric antennas can be cofire-integrated into CCS 302. The antennas of different configurations can receive and/or transmit signals having different wave patterns, frequencies, polarities, or other different characteristics to provide for antenna diversity. As such, depending on the external device to which antenna 304 is communicating in a particular environment, which can change from time to time, a particular antenna of multiple antennas cofire-integrated into a single CCS can be employed for communication.

In some embodiments, electrical circuitry 308 may include one or more components or modules configured to perform an electrical function. By way of example, but not limitation, electrical circuitry 308 may include a communication module (e.g., transmitter, receiver and/or transceiver) configured to output a signal via antenna 304, sensing module configured to sense a physiological or biological signal of human body 110, a therapy module configured to generate and deliver an electrical stimulation therapy to human body 110 or to generate a signal causing IMD 300 to output medication to the body of the wearer of IMD 300 or the like. In various embodiments, electrical circuitry 308 can include circuitry for one or more of an implantable sensor, an implantable therapy lead, an implantable monitor, an implantable cardioverter defibrillator, an implantable neurostimulator, an implantable physiological monitor and/or an implantable pulse generator. Sensors described herein can include sensors of different organs and physiological components including, but not limited to, lung, spine, eyes, heart, brain and/or nerve sensors.

IMD 300 can be subcutaneously implanted within skin, fat and/or muscle of human body 110, swallowed and/or injected into the bloodstream of human body 110. Further, although human body 110 is shown, CCS 302 can also be provided within other types of structures (e.g., animal body) in these embodiments.

CCS 302 can be electrically coupled and/or communicatively coupled to electrical circuitry 308 such that communication circuitry is electrically coupled and/or communicatively coupled to antenna 304. For example, electrical and/or communicative coupling can occur via a feedpoint (not shown in FIG. 3) of CCS 302. In some embodiments, CCS 302 and electrical circuitry 308 can be electrically coupled via a feedthrough (not shown in FIG. 3) of CCS 302. By way of example, but not limitation, electrical circuitry 308 can include one or more of an RF module, a controller, a processor, a memory, data storage or the like. As such, one or more operations of medical device telemetry system 100, 102' and/or of the embodiments of IMDs described herein can be facilitated.

IMD 300 can be an implantable device configured to output an electrical signal to human body 110 and/or monitor fluid, nerves, organ activity and/or other physiological condition (e.g., level of cholesterol, level of serotonin) of human body 110. Examples of IMD 300 can include, but is not limited to, pacemakers, implantable neurostimulators, implantable cardioverter defibrillators, implantable physiological monitors and/or implantable therapy leads.

As shown in FIG. 3, CCS 302 can include hollow cavity 312 through a portion of CCS 302. For example, hollow cavity 312 may be open at one end to form a hollow cap configuration. Such a configuration will be described in further detail with respect to FIGS. 4 and 5.

CCS 302 can be adjoined to housing 306 in some embodiments. As such, the combination of CCS 302 and housing 306 enclose and hermetically seal electronic components 308 and power source 310 from bodily tissue and fluids. In this embodiment, CCS 302 is exposed to the bodily tissues and fluids of patient 110 when implanted. CCS 302 may be sized to align with the portion of housing 306 to which it is coupled such that there are not sharp edges at the transition point from CCS 302 to housing 306. CCS 302 can be adjoined to housing 306 at the open end of CCS 302. CCS 302 and housing 306 may be adjoined via any of a number of techniques, e.g., via an adhesive, via welding or other process. In some embodiments, CCS 302 can be directly joined to housing 306 with no additional components (e.g., device headers, caps). In other embodiments, CCS 302 may be covered by an additional housing component such that CCS 302 is not exposed to the bodily tissues and fluids of patient 110 when implanted. Accordingly, housing 306 can shield the body from CCS 302 thereby minimizing leakage of materials from, and/or body fluid ingress into, CCS 302 and/or antenna 304. Placing CCS 302 inside housing 306 can also minimize body immune response to CCS 302.

Housing 306 may, in some instances, be formed of a conductive material (or metal), such as titanium. In this case, the dielectric material from which CCS 302 is formed (e.g., ceramic) electrically isolates antenna 304 from the conductive housing 306. In other instances, housing 306 can be formed of a polymeric material. In such embodiments, CCS 302 can be encapsulated in housing 306 in lieu of being adjoined to housing 306, as a metal housing may block RF signals from reaching the antenna.

In various embodiments, housing 306 and CCS 302 are adjoined to one another. For example, in some embodiments, housing 306 and CCS 302 are adjoined to one another via a seal. In some embodiments, the seal is a hermetic seal. In some embodiments, housing 306 and CCS 302 are individually hermetically sealed and then adjoined to one another. The hermetic seal can be provided via any number of methods for providing hermetic seals including, but not limited to, brazing, soldering, welding, compression sealing, glass sealing, diffusion bonding and/or epoxy sealing. In some embodiments, a conductive material can be cofired around the edges of CCS 302. The conductive material can then be welded to housing 306 in some embodiments.

In some embodiments, one or more seals employed can be non-hermetic seals (e.g., plastic encapsulation). For example, in embodiments in which CCS 302, antenna 304, a feedthrough (not shown) and/or IMD 300 are composed of biostable and biocompatible materials and/or in which housing 306 and CCS 302 are individually hermetically sealed, housing 306 and CCS 302 can be adjoined by a non-hermetic seal.

In various embodiments, housing 306, or one or more components of housing 306, can be electrically coupled to CCS 302, including coupling to antenna 304, capacitively or via feedthrough to perform one or more functions of components of housing 306 and/or CCS 302. For example, operations of antenna 304 can be facilitated via capacitive or electrical coupling between CCS 302 and components of housing 306.

In some embodiments, housing 306 and CCS 302 can be electrically coupled to one another via a feedthrough. One or more portions of feedthrough can be cofire-integrated in CCS 302 in various embodiments.

As shown, CCS 302 is not encapsulated by a housing and, as such, upon implantation, is in direct contact with human body tissue and/or human body fluid. As such, in some embodiments, CCS 302 and/or antenna 304 can be composed of biostable and/or biocompatible materials. In some embodiments, biostable and/or biocompatible material can be employed for the outermost layer of materials from which CCS 302 and/or antenna 304 are formed. As such, portions of CCS 302 and/or antenna 304 most likely to contact human body tissue and/or human body fluid can be composed of biostable and/or biocompatible material.

Figure 4A:
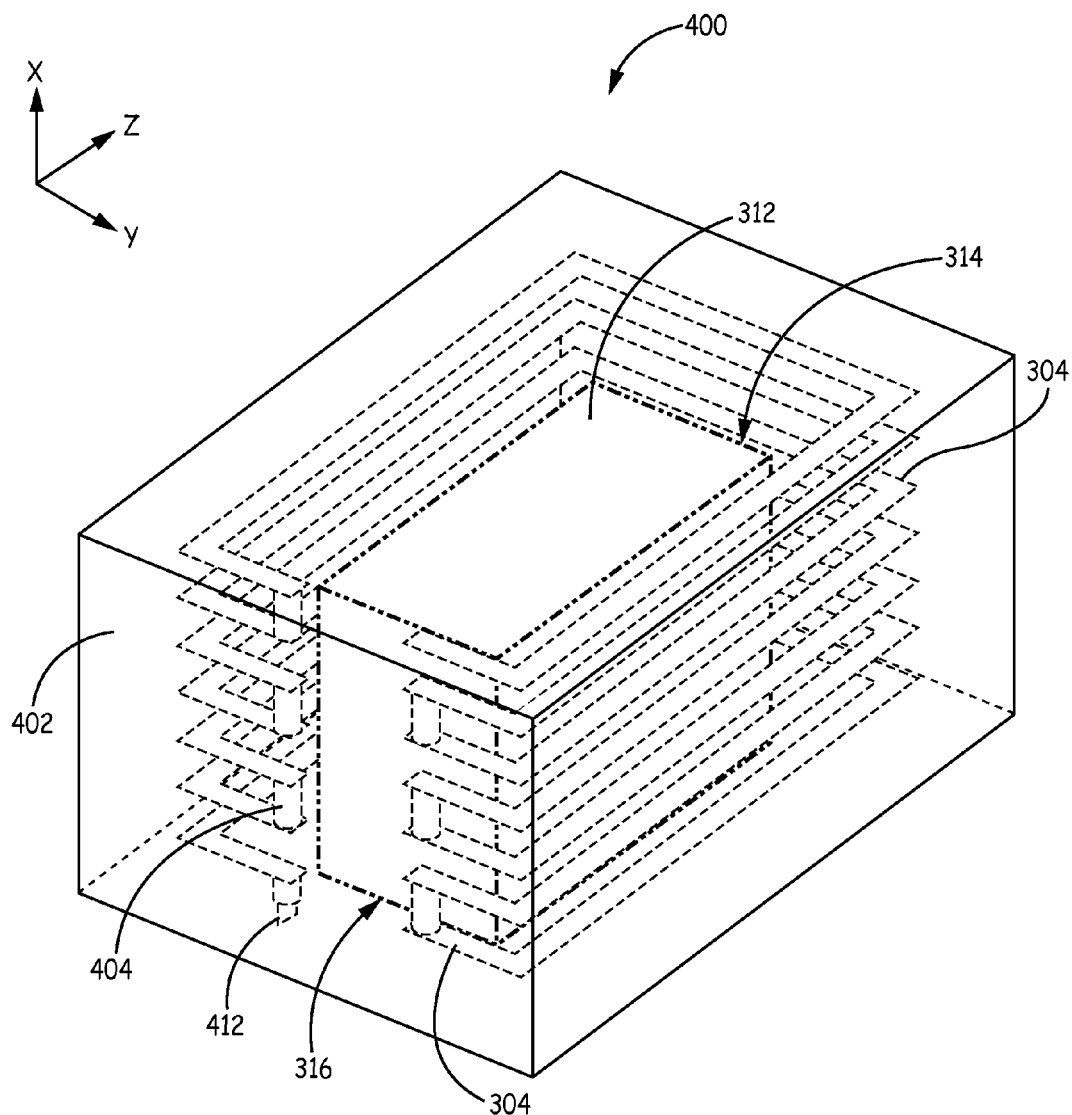
FIG. 4A illustrates a perspective view of an exemplary non-limiting CCS having a partially hollow cavity and substantially serpentine-shaped antenna in accordance with embodiments described herein.

FIG. 4A illustrates a perspective view of an exemplary non-limiting CCS having a partially hollow cavity and substantially serpentine-shaped antenna in accordance with embodiments described herein. In various embodiments, CCS 400 can include one or more of the structure and/or functionality of CCS 302 (and vice versa). Repetitive description of like elements employed in other embodiments is omitted for sake of brevity.

Antenna 304 is cofire-integrated into wall 402 of CCS 400. CCS 400 can be formed, for example, according to a fabrication process as described below or other fabrication process. After cofiring, CCS 400, for example, can include multiple layers and conductive traces that are formed in a generally rectangular shape with a space between the ends on a plurality of the layers. Each of the traces can be separated from one another by layers of dielectric and vias can be formed between layers to interconnect the conductive traces to form the serpentine shape. As illustrated in FIG. 4A, the vias interconnecting the layers of conductive traces are located on opposite ends of the traces at each subsequent layer. For example, looking at the front of CCS 400, the uppermost via 404 connects the left ends of the uppermost conductive trace and the next subsequent conductive trace, the next via toward the bottom of CCS 400 connects the right ends is located on the right ends of the two layers of conductive traces, and so on and so forth along the progression of layers to form the generally serpentine shape.

In various embodiments, material from which feedpoint 412 is composed can be provided in or on one or more of the dielectric layer to form feedpoint 412 upon cofiring. Feedpoint 412 can provide conductivity between antenna 304 and one or more components in housing 306.

While antenna 304 is substantially serpentine-shaped, in various embodiments, any number of other configurations of three-dimensional antennas can be employed. For example, as described with reference to FIGS. 5A-5E, antenna 304 can be substantially helical-shaped. As shown, in various embodiments, conductive material can be embedded in dielectric material from which CCS 400 is composed to create vias 404 connecting portions of antenna 304 across regions or layers of CCS 400.

CCS 400 is formed such that one or more walls 402 define a hollow cavity 312. CCS 400 includes four walls 402 that form a generally rectangular shape. However, CCS 400 may be formed into other shapes such as a square shape, circular shape, oval shape, or other shape. The number of walls 402 is dependent upon the desired shape of CCS 400. CCS 400 also includes a wall 402 along a top of CCS 400 (e.g., functioning as a ceiling). Hollow cavity 312 of FIG. 4A includes two ends 314, 316. End 314 abuts up to wall 402 along the top of CCS 400, thus forming a closed end of CCS 400. As such, hollow cavity 312 cannot be accessed via the closed end. End 316, on the other hand, is open to provide access to hollow cavity 312. In these embodiments, the base of wall 402 located near open end 316 can be coupled to a housing (e.g., housing 306 of FIG. 3). In this embodiment, dielectric material from which CCS 400 is formed can electrically isolate antenna 304 from the housing (which, in some embodiments, can be formed of metal).

Figure 4B:
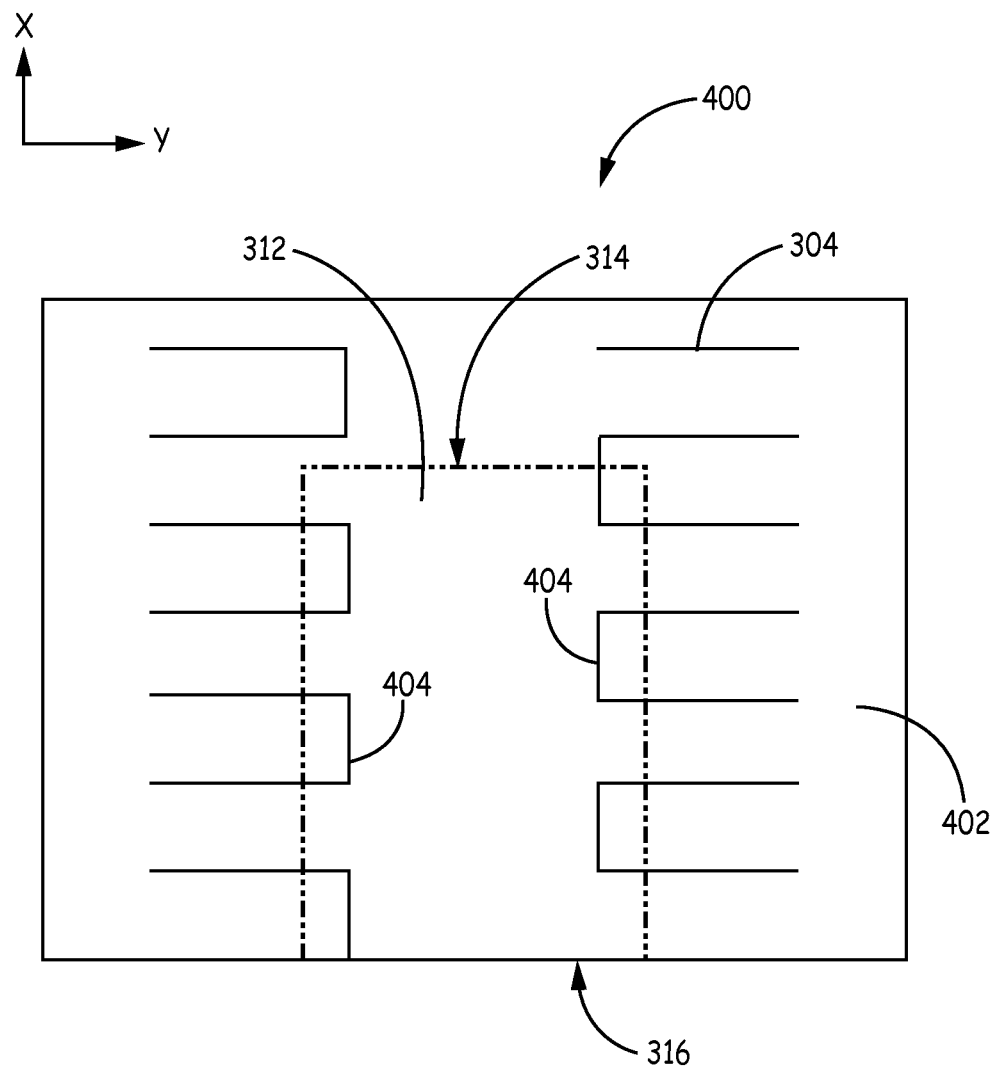
FIG. 4B illustrates a front view of an exemplary non-limiting CCS having a partially hollow cavity and substantially serpentine-shaped antenna in accordance with embodiments described herein.

FIG. 4B illustrates a front view of CCS 400 of FIG. 4A having a partially hollow cavity and substantially serpentine-shaped antenna in accordance with embodiments described herein. As shown, antenna 304 is cofire-integrated into wall 402 of CCS 400. As shown in FIGS. 4B, 4D and 4E, portions of antenna 304 are also provided in front of hollow cavity 312. Each layer of conductive traces has a space between the ends of the conductive traces on that layer with via 404 extending from one of the ends of the conductive traces through the dielectric layers to the subsequent conductive trace.

For clarity, the outline of hollow cavity 312 is illustrated with a dotted line pattern and regions of antenna 304 are provided in front of hollow cavity 312. While hollow cavity 312 is shown with dotted lines to represent the surface forming hollow cavity 312, in some embodiments, hollow cavity 312 does not protrude through the entirety of wall 402 from front to back. Rather, hollow cavity 312 represents an air core through an interior region of CCS 400.

Figure 4C:
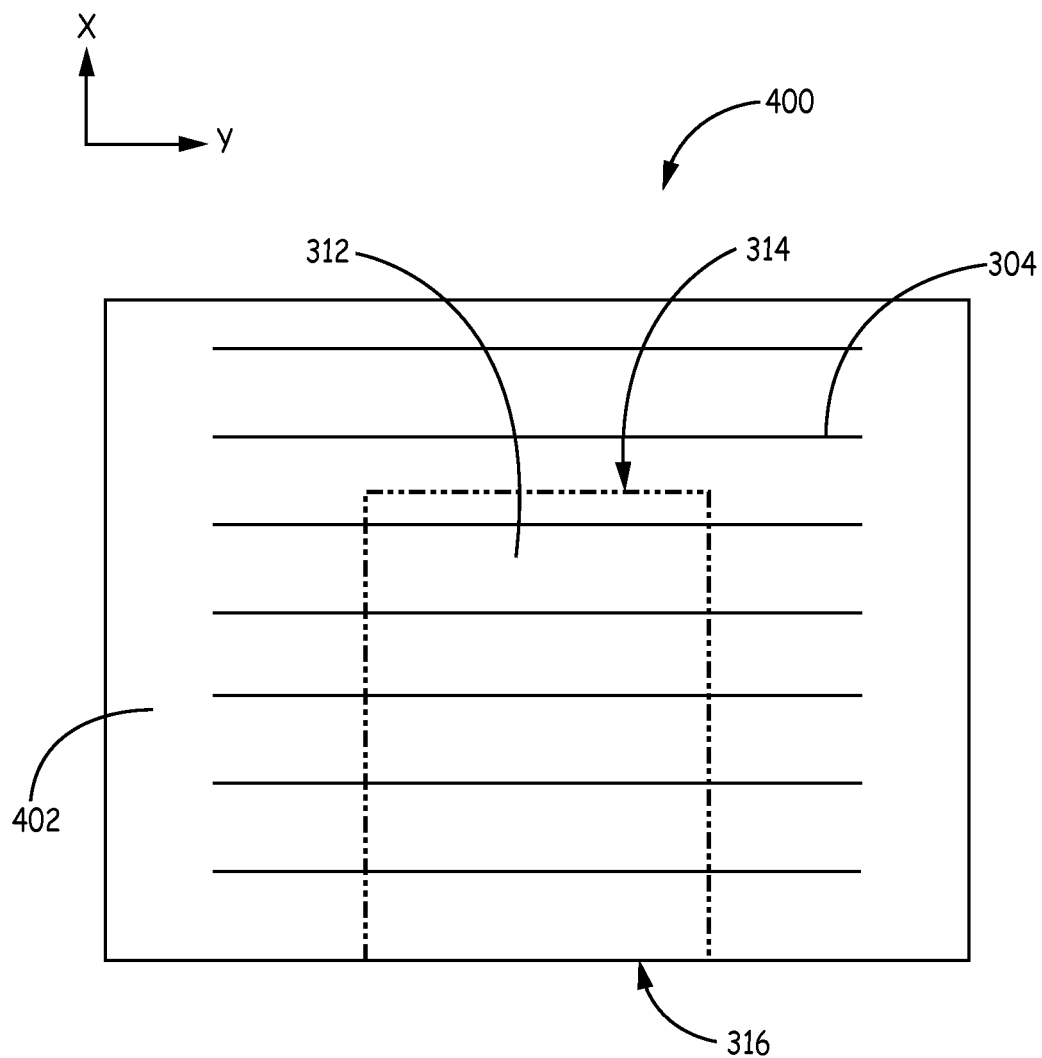
FIG. 4C illustrates a back view of an exemplary non-limiting CCS having a partially hollow cavity and substantially serpentine-shaped antenna in accordance with embodiments described herein.
Figure 4D:
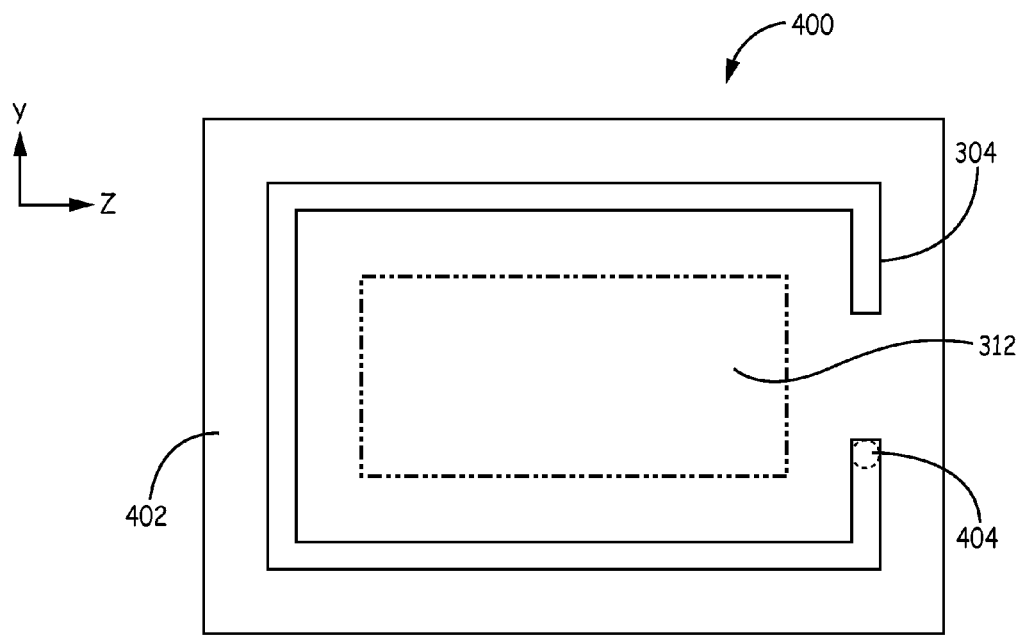
FIG. 4D illustrates a top view of an exemplary non-limiting CCS having a partially hollow cavity and substantially serpentine-shaped antenna in accordance with embodiments described herein.
Figure 4E:
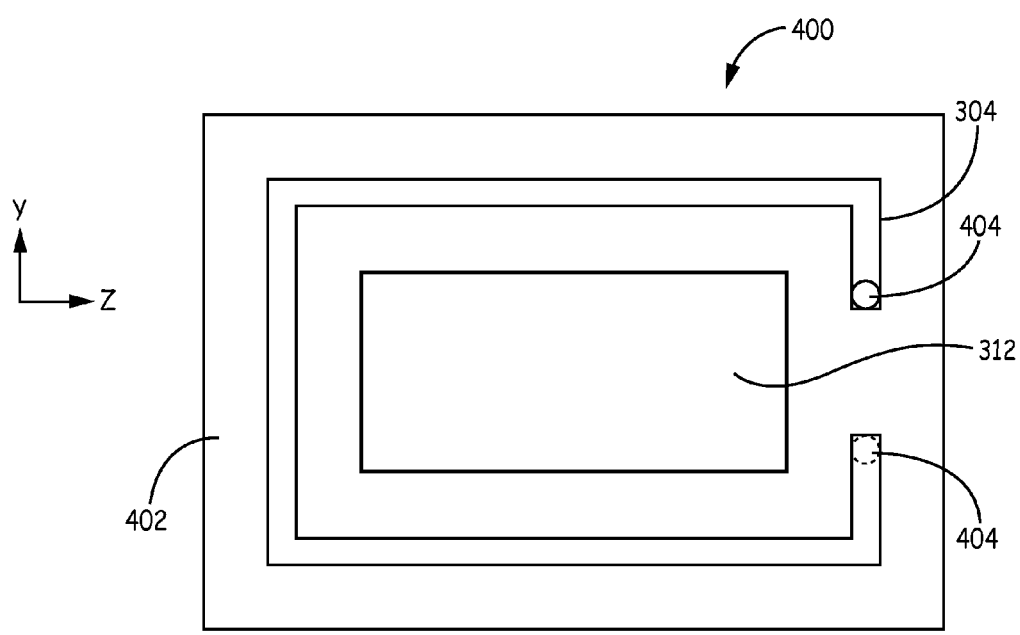
FIG. 4E illustrates a bottom view of an exemplary non-limiting CCS having a partially hollow cavity and substantially serpentine-shaped antenna in accordance with embodiments described herein.

FIG. 4C illustrates a back view of CCS 400 of FIG. 4A having partially hollow cavity 312 and substantially serpentine-shaped antenna 304 in accordance with embodiments described herein. As shown, antenna 304 is cofire-integrated into wall 402 of CCS 400. The conductive traces of each of the layers extends across a substantial portion of the wall 402 illustrated in the back view of FIG. 4C.

FIG. 4D illustrates a top view of CCS 400 of FIG. 4A having partially hollow cavity 312 and substantially serpentine-shaped antenna 304 in accordance with embodiments described herein. In particular, FIG. 4D shows a top view of the uppermost layer of CCS 400 that includes conductive traces of antenna 304. One or more additional layers of dielectric material may reside over the illustrated layer such that the conductive traces forming antenna 304 are not exposed to bodily tissue or fluid. In the embodiment shown, hollow cavity 312 does not protrude through the entirety of CCS 400 and, as such, is shown with a dotted line to represent the shape of hollow cavity 312 within CCS 400 from the top view of CCS 400.

As illustrated in FIG. 4D, the conductive trace forming portion of antenna 304 is formed in a generally rectangular shape within the dielectric material of walls 402. In particular, the conductive trace begins at a front wall 402, extends partially across the front wall 402, extends along a first side wall 402, along a back wall 402, along a second side wall 402, and then partially along the opposite side of the front wall 402 as the starting point of the trace. As illustrated in FIG. 4D, the beginning and end of the conductive trace are spaced apart from one another along the front wall 402. A conductive via 404 extends from one of the end of the conductive trace through the dielectric layers to another conductive trace on a different layer to electrically couple the conductive traces of the different layers. Conductive via 404 is shown as a dotted line because it extends below the conductive trace.

FIG. 4E illustrates a bottom view of CCS 400 of FIG. 4A having partially hollow cavity 312 and substantially serpentine-shaped antenna 304 in accordance with embodiments described herein. In particular, FIG. 4D shows the bottommost layer of CCS 400 that includes conductive traces of antenna 304. One or more additional layers of dielectric material may reside below the illustrated layer such that the conductive traces forming antenna 304 are not located on an outermost layer of CCS 400. Hollow cavity 312 is shown with solid line to indicate that the bottom end of hollow cavity 312 is open to provide access to hollow cavity 312 and thus, is present from the bottom view of CCS 400. As described above, the bottom of hollow cavity 312 can provide an area for incorporating portion of the electronic circuitry or other components of an IMD to which CCS 400 is coupled. Alternatively, hollow cavity 32 can provide a point of entry for feedthrough or any number of other connections (e.g., metal pad) between antenna 302 and a component in a housing of an IMD to which CCS 400 is coupled.

As illustrated in FIG. 4E, the conductive trace forming portion of antenna 304 is formed in a generally rectangular shape within the dielectric material of walls 402. In particular, the conductive trace begins at a front wall 402, extends partially across the front wall 402, extends along a first side wall 402, along a back wall 402, along a second side wall 402, and then partially along the opposite side of the front wall 402 as the starting point of the trace. As illustrated in FIG. 4E, the beginning and end of the conductive trace are spaced apart from one another along the front wall 402. A first conductive via 404 (illustrated in a solid line) extends from one end of the conductive trace upward through the dielectric layers to another conductive trace on a different layer to electrically couple the conductive traces of the different layers to form antenna 304. A second conductive via 404 (illustrated as a dotted line) extends downward to electrically couple the conductive trace with a feedpoint 412 (not shown in FIG. 4E).

Figure 5A:
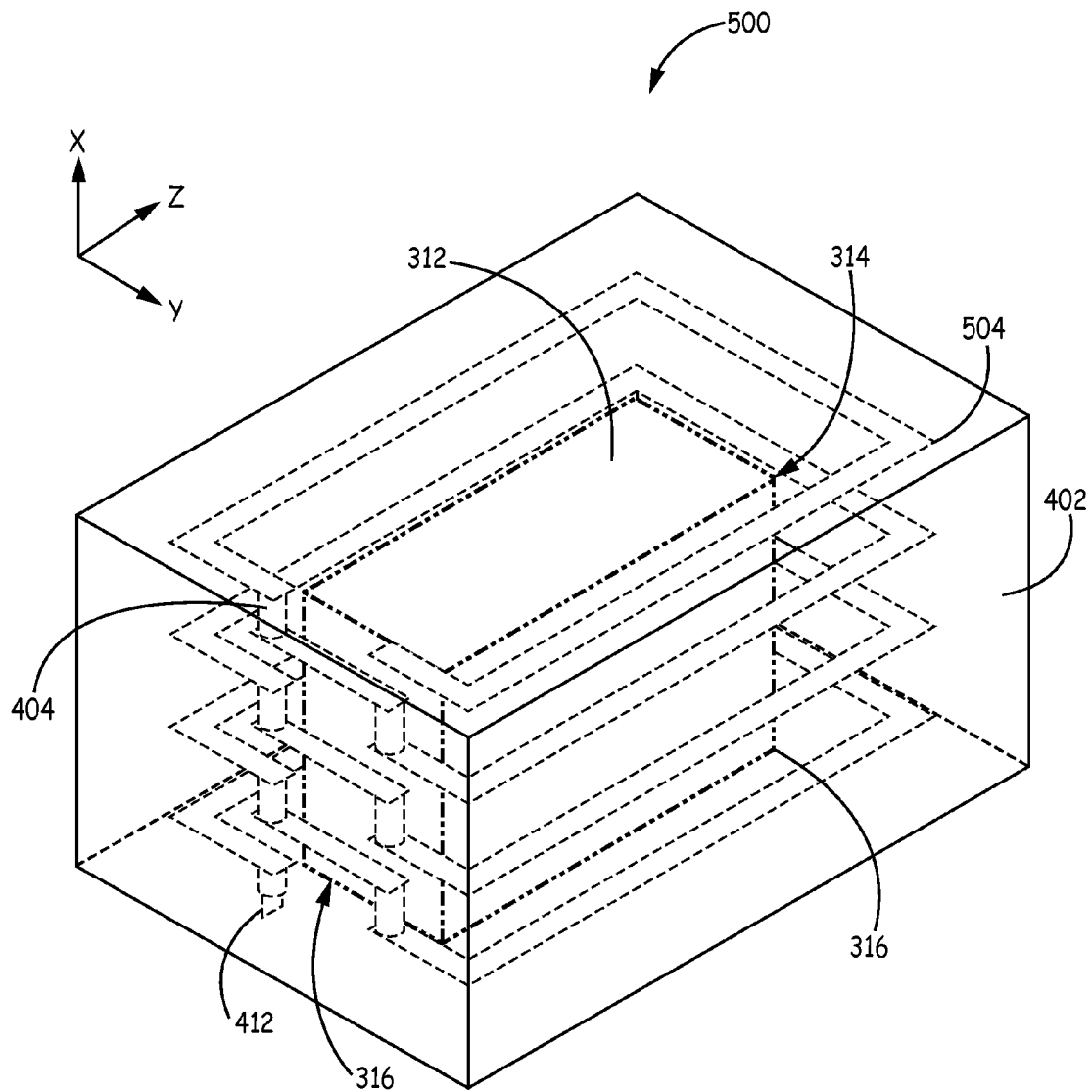
FIG. 5A illustrates a perspective view of an exemplary non-limiting CCS having a partially hollow cavity and substantially helical-shaped antenna in accordance with embodiments described herein.

FIG. 5A illustrates a perspective view of an exemplary non-limiting CCS 500 having a partially hollow cavity 312 and substantially helical-shaped antenna 504 in accordance with embodiments described herein. In various embodiments, CCS 500 can include one or more of the structure and/or functionality of CCS 302, 400 (and vice versa). Repetitive description of like elements employed in other embodiments is omitted for sake of brevity.

Antenna 504 is cofire-integrated into walls 402 of CCS 500. In the embodiment shown, antenna 504 is substantially helical-shaped. After cofiring, CCS 500, for example, can include multiple layers and conductive traces that are formed in a generally rectangular shape with a space between the ends on a plurality of the layers. Between each of the layers of rectangular shaped conductive traces are layers are straight conductive traces that are aligned with the open space between the ends of the rectangular shaped conductive traces in the x-direction and extend substantially the length of the open space. In other words, the straight conductive traces extend far enough such that the ends of the straight conductive traces overlap the ends of the rectangular conductive traces in the x-direction, e.g., along the height of the component. Each of the traces can be separated from one another by layers of dielectric and vias can be formed through the dielectric layers to interconnect the conductive traces to form the helical-shape thereby forming antenna 504 and CCS 500 after cofiring.

Each of the layers of traces is separated from other layers of traces by vias 404 formed to interconnect the conductive traces of subsequent layers to form the generally helical-shaped antenna 504. As illustrated in FIG. 5A and the front view in FIG. 5B, a via 404 extends from a first end of rectangular traces and interconnects with a first end of the straight conductive trace of a subsequent layer of traces (e.g., a left end of each of the traces as is the case in the uppermost section of antenna 504 of FIG. 5A). A second via 404 extends from a second end of the straight conductive trace (e.g., opposite the end of the first via 404) to an end of a second rectangular conductive trace of a further subsequent layer (e.g., the third layer of traces from the top of CCS 500 in FIG. 5A). The end of the second rectangular conductive trace is the opposite end of the open space that the via of the first rectangular conductive trace is interconnected with. More specifically, with respect to FIGS. 5A and 5B, the first via connects the end of the first, uppermost rectangle conductive trace on the left-hand side (as viewed from the front of CCS 500) to the end of the straight conductive trace on the left-hand side and the second via connects the end of the straight conductive trace on the right-hand side to the end of the second rectangle conductive trace on the right-hand side (as viewed from the front of CCS 500). The pattern then repeats through the progression of layers to form the helical-shaped antenna 504.

Figure 5B:
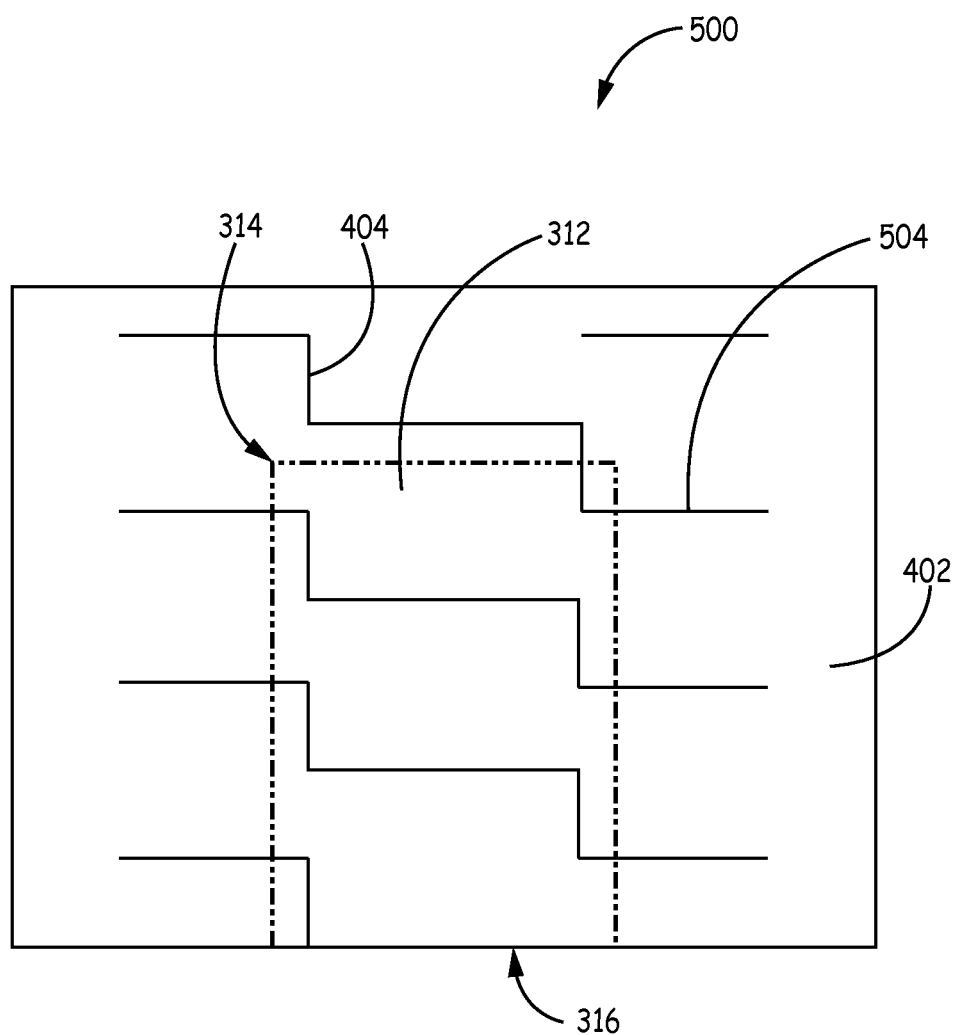
FIG. 5B illustrates a front view of an exemplary non-limiting CCS having a partially hollow cavity and substantially helical-shaped antenna in accordance with embodiments described herein.

FIG. 5B illustrates a front view of an exemplary non-limiting CCS 500 having partially hollow cavity 312 and substantially helical-shaped antenna 504 in accordance with embodiments described herein. For clarity, the outline of hollow cavity 312 is illustrated with a dotted line pattern and regions of antenna 504 are provided in the wall 402 in front of hollow cavity 312 (not within the hollow cavity itself). While hollow cavity 312 is shown with dotted lines to represent the surface forming hollow cavity 312, in some embodiments, hollow cavity 312 does not protrude through the entirety of wall 402 from front to back. Rather, hollow cavity 312 represents an air core through an interior region of CCS 500.

Figure 5C:
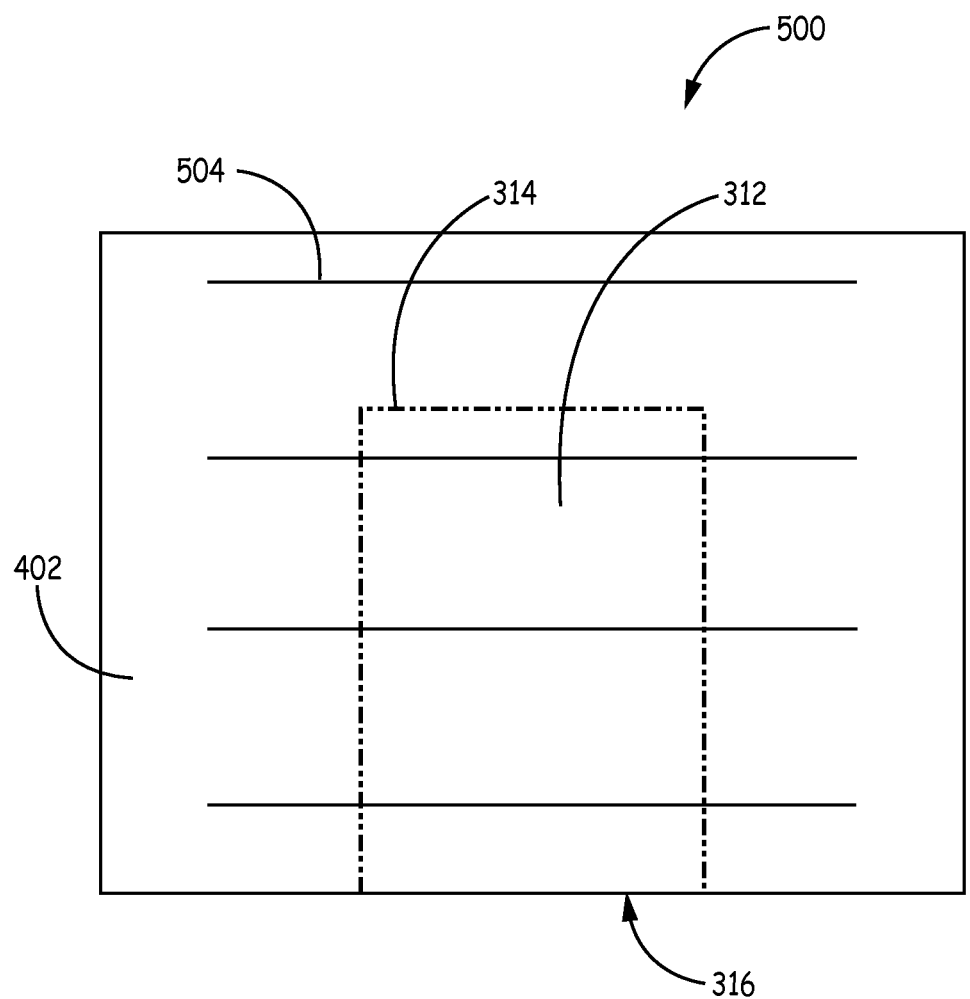
FIG. 5C illustrates a back view of an exemplary non-limiting CCS having a partially hollow cavity and substantially helical-shaped antenna in accordance with embodiments described herein.

FIG. 5C illustrates a back view of an exemplary non-limiting CCS 500 having partially hollow cavity 312 and substantially helical-shaped antenna 504 in accordance with embodiments described herein. As shown, antenna 504 can be provided in wall 402 of CCS 500. Again, the outline of hollow cavity 312 is illustrated with a dotted line pattern and regions of antenna 504 are provided in the wall 402 in front of hollow cavity 312 (not within the hollow cavity itself). The conductive traces of each of the layers extends across a substantial portion of the wall 402 illustrated in the back view of FIG. 5C. Further, in this embodiment, as with embodiments of FIGS. 4A-4E, end 314 of hollow cavity 312 is closed while end 316 of hollow cavity 312 is open to provide access to hollow cavity 312.

Figure 5D:
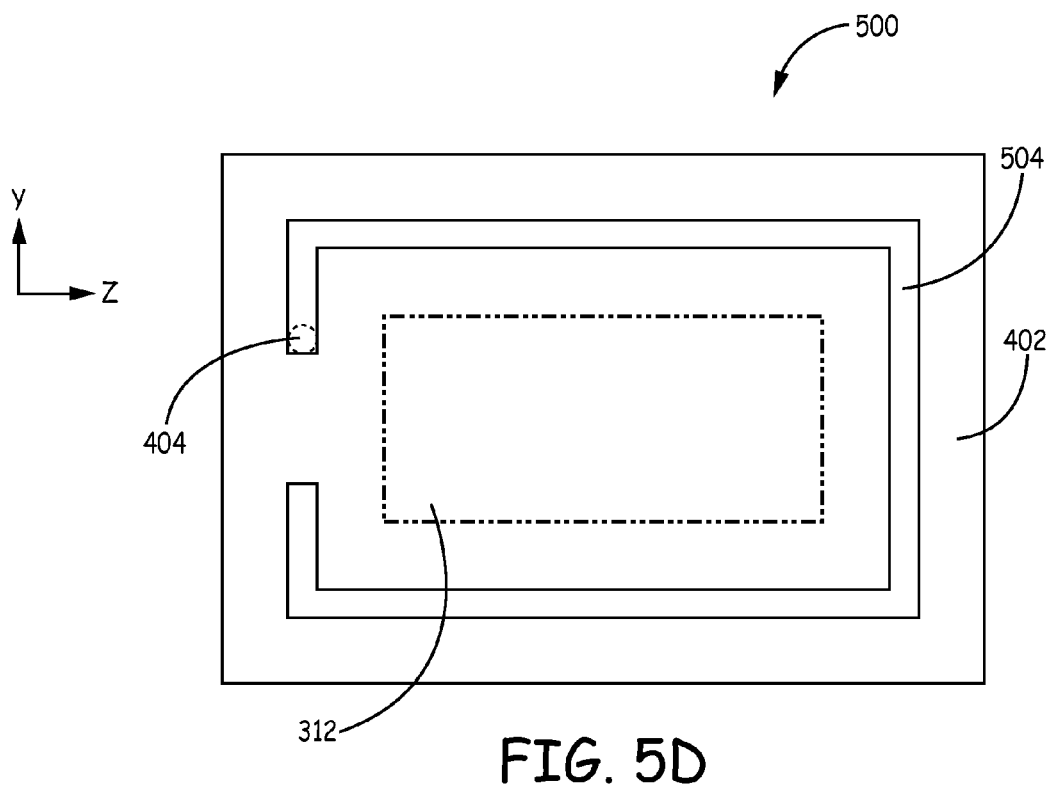
FIG. 5D illustrates a top view of an exemplary non-limiting CCS having a partially hollow cavity and substantially helical-shaped antenna in accordance with embodiments described herein.

FIG. 5D illustrates a top view of an exemplary non-limiting CCS 500 having partially hollow cavity 312 and substantially helical-shaped antenna 504 in accordance with embodiments described herein. In particular, FIG. 5D shows a top view of the uppermost layer of CCS 500 that includes conductive traces of antenna 504. One or more additional layers of dielectric material may reside over the illustrated layer such that the conductive traces forming antenna 504 are not exposed to bodily tissue or fluid.

Figure 5E:
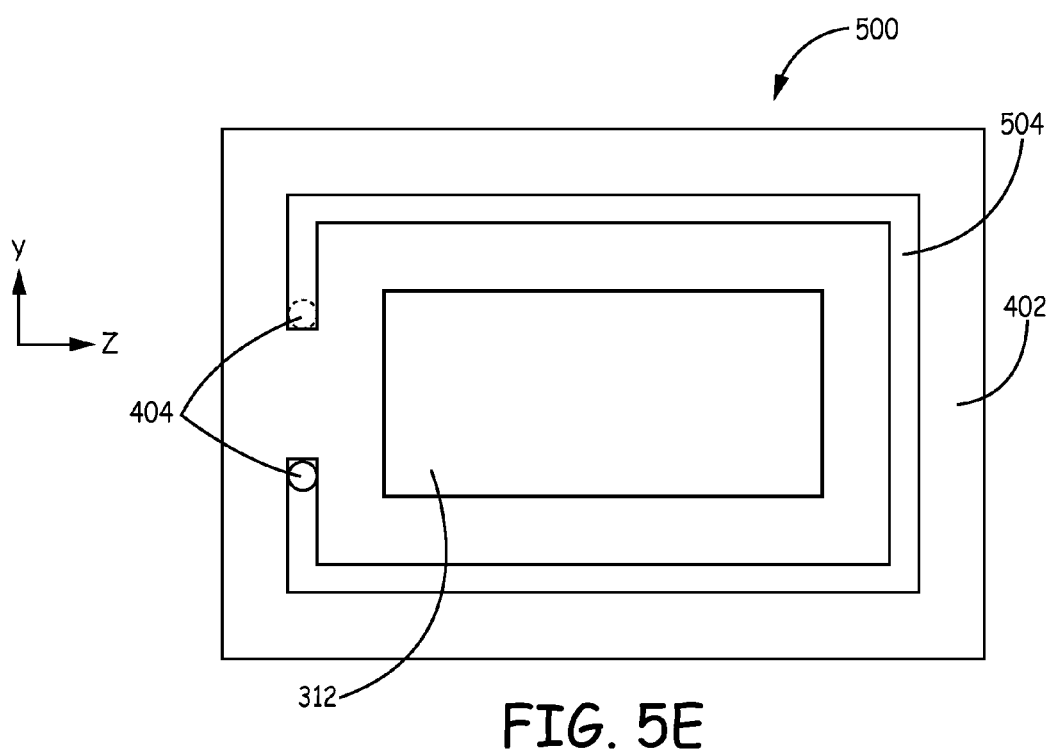
FIG. 5E illustrates a bottom view of an exemplary non-limiting CCS having a partially hollow cavity and substantially helical-shaped antenna in accordance with embodiments described herein.

FIG. 5E illustrates a bottom view of an exemplary non-limiting CCS 500 having partially hollow cavity 312 and substantially helical-shaped antenna 504 in accordance with embodiments described herein. In particular, FIG. 5D shows the bottommost layer of CCS 500 that includes conductive traces of antenna 504. One or more additional layers of dielectric material may reside below the illustrated layer such that the conductive traces forming antenna 504 are not located on an outermost layer of CCS 500.

The conductive trace forming portion of antenna 504 illustrated in FIGS. 5D and 5E are formed in a generally rectangular shape within the dielectric material of walls 402. In particular, the conductive trace begins at a front wall 402, extends partially across the front wall 402, extends along a first side wall 402, along a back wall 402, along a second side wall 402, and then partially along the opposite side of the front wall 402 as the starting point of the trace. As illustrated in FIG. 4D, the beginning and end of the conductive trace are spaced apart from one another along the front wall 402.

Figure 6:
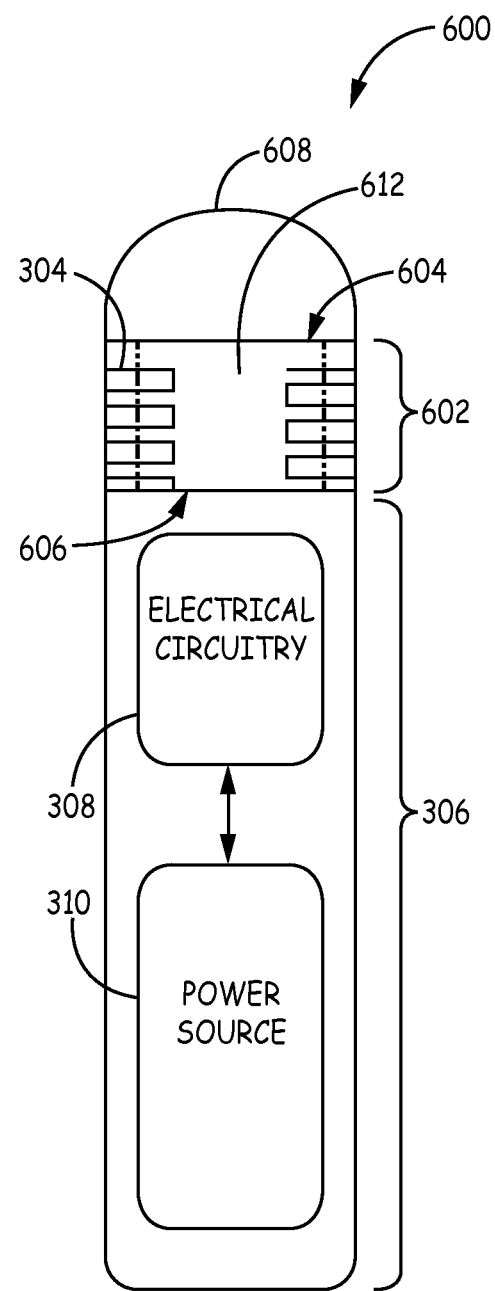
FIG. 6 illustrates a cross-sectional view of an exemplary non-limiting IMD having a cap covering the CCS in accordance with embodiments described herein.

FIG. 6 illustrates a cross-sectional view of an exemplary non-limiting IMD 600 having CCS 602 that is formed into a hollow sleeve in accordance with embodiments described herein. In various embodiments, IMD 600 can include one or more of the structure and/or functionality of IMD 102, 200, 300 (and vice versa). Repetitive description of like elements employed in other embodiments is omitted for sake of brevity.

CCS 602 includes an antenna embedded within CCS 602. In the example illustrated in FIGS. 6 and 7A, the antenna is illustrated as being a substantially serpentine-shaped antenna 304 described in detail above with respect to FIGS. 3 and 4A-E. Although antenna 304 is similar to that described above with respect to FIGS. 3 and 4A-E, CCS 602 is different in that it includes a hollow cavity 612 that extends through the entire length of CCS 602 such that CCS 602 may be viewed as a hollow sleeve.

CCS 602 can be adjoined to housing 306 at one end of CCS 602, and a second housing portion, such as cap 608, is adjoined to the second end of CCS 602. The adjoining may be accomplished using an adhesive, via welding or other process. As such, the combination of CCS 602, housing 306, and cap 608 enclose and hermetically seal electronic components 308 and power source 310 from bodily tissue and fluids. In this embodiment, CCS 602 is exposed to the bodily tissues and fluids of patient 110 when implanted. In other instances, the cap 608 may encapsulates some or all of CCS 602. IMD 600 can also include electrical circuitry 308 and power source 310 configured to power IMD 600 (or one or more components of IMD 600). In various embodiments, one or more of CCS 602 having cofire-integrated antenna 304 embedded in CCS 602, housing 306, electrical circuitry 308 and/or power source 310 can be communicatively and/or electrically coupled to one another to perform one or more functions of IMD 600.

In the embodiment shown, ends 604, 606 of hollow cavity 612 are open. In other words, hollow cavity 612 can be accessed via either of the ends 604 or 606 of CCD 602. As such, in this embodiment, CCS 602 is formed as a ceramic sleeve having antenna 304 in the wall of the sleeve. Accordingly, to avoid exposure to bodily fluids and/or gases, of components that can be placed in hollow cavity 612, cap 608 can be provided over end 604 as shown. Hollow cavity 612 may allow for one or more electronic components of IMD 600 to extend within the cavity thus advantageously increasing efficiency through utilization of the hollow cavity for components. The hollow cavity can provide low dielectric properties because the lower dielectric constant of the cavity provides improved isolation of the electrical circuit placed inside the cavity, reducing coupling to the antenna and thus minimally impacting the antenna performance. This attribute enables closer separation distances between the antenna and associated electrical circuitry and higher system packaging density and miniaturization. Moreover, placement of components within the hollow cavity of the ceramic structure can further reduce the size of the IMD since the number of components within the housing of the IMD can be reduced.

Cap 608 can be adjoined to or integrally formed with CCS 602. For example, in some embodiments, cap 608 can be cofire-integrated with materials forming CCS 602 to fabricate a single structure. In other embodiments, cap 608 can be sealed to CCS 602 employing a hermetic sealing method. For example, cap 608 can be hermetically sealed to CCS 602 by metal brazing, glass joining or diffusion bonding approaches.

Figure 7A:
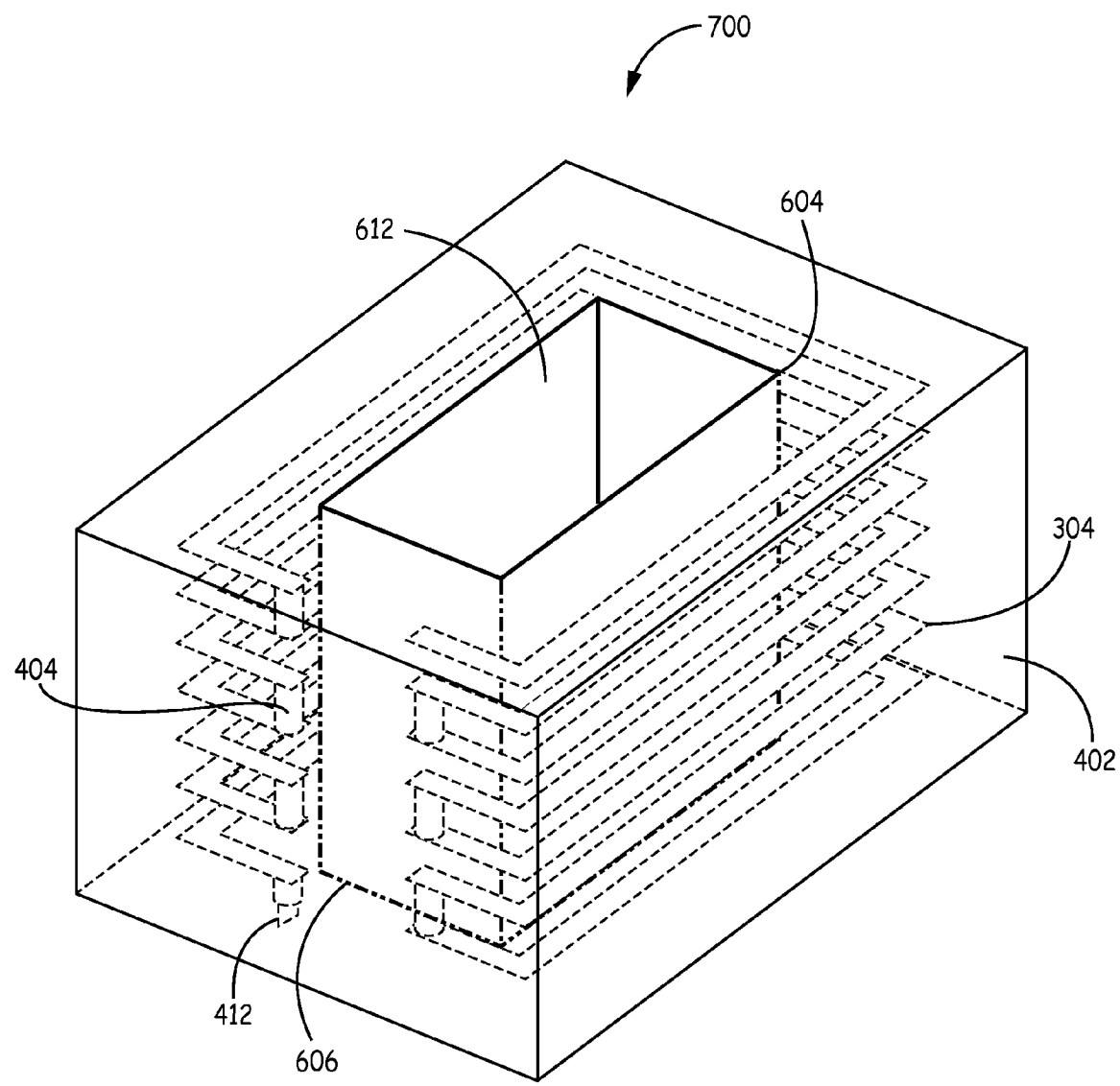
FIG. 7A illustrates a perspective view of an exemplary non-limiting CCS having a hollow cavity and substantially serpentine-shaped antenna in accordance with embodiments described herein.

FIG. 7A illustrates a perspective view of an exemplary non-limiting CCS 700 having a hollow cavity 612 and substantially serpentine-shaped antenna 304 in accordance with embodiments described herein. In various embodiments, CCS 700 can include one or more of the structure and/or functionality of CCS 302, 400, 500 (and vice versa). Repetitive description of like elements employed in other embodiments is omitted for sake of brevity.

In the embodiment shown, hollow cavity 612 protrudes through each end of CCS 700 causing CCS 700 to form a sleeve structure. Accordingly, while FIGS. 4A-4E and 5A-5E illustrated embodiments of CCSs with one open end and one closed end, FIGS. 7A-7E illustrate embodiments of a CCS (e.g., CCS 700) with two open ends such that cavity 612 extends all the way through CCS 700.

Figure 7B:
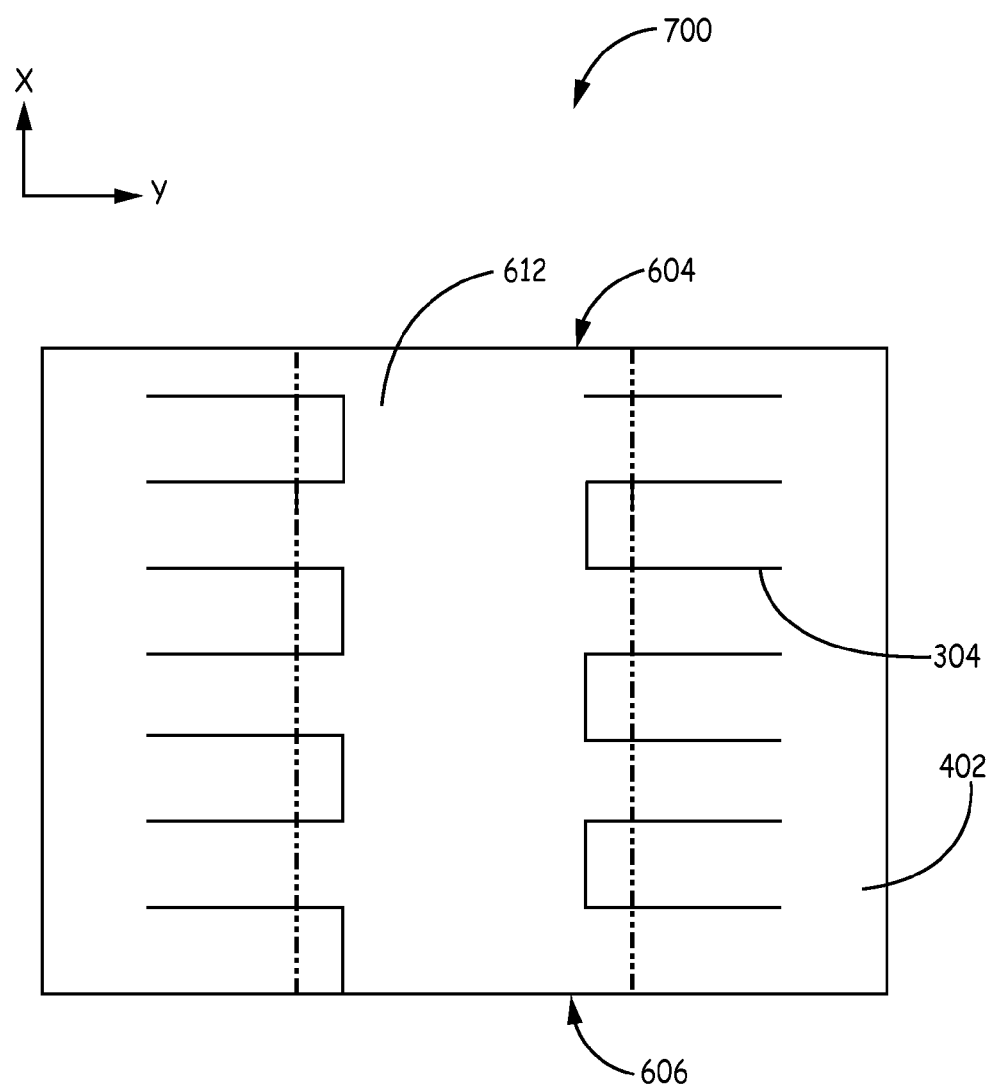
FIG. 7B illustrates a front view of an exemplary non-limiting CCS having a hollow cavity and substantially serpentine-shaped antenna in accordance with embodiments described herein.
Figure 7C:
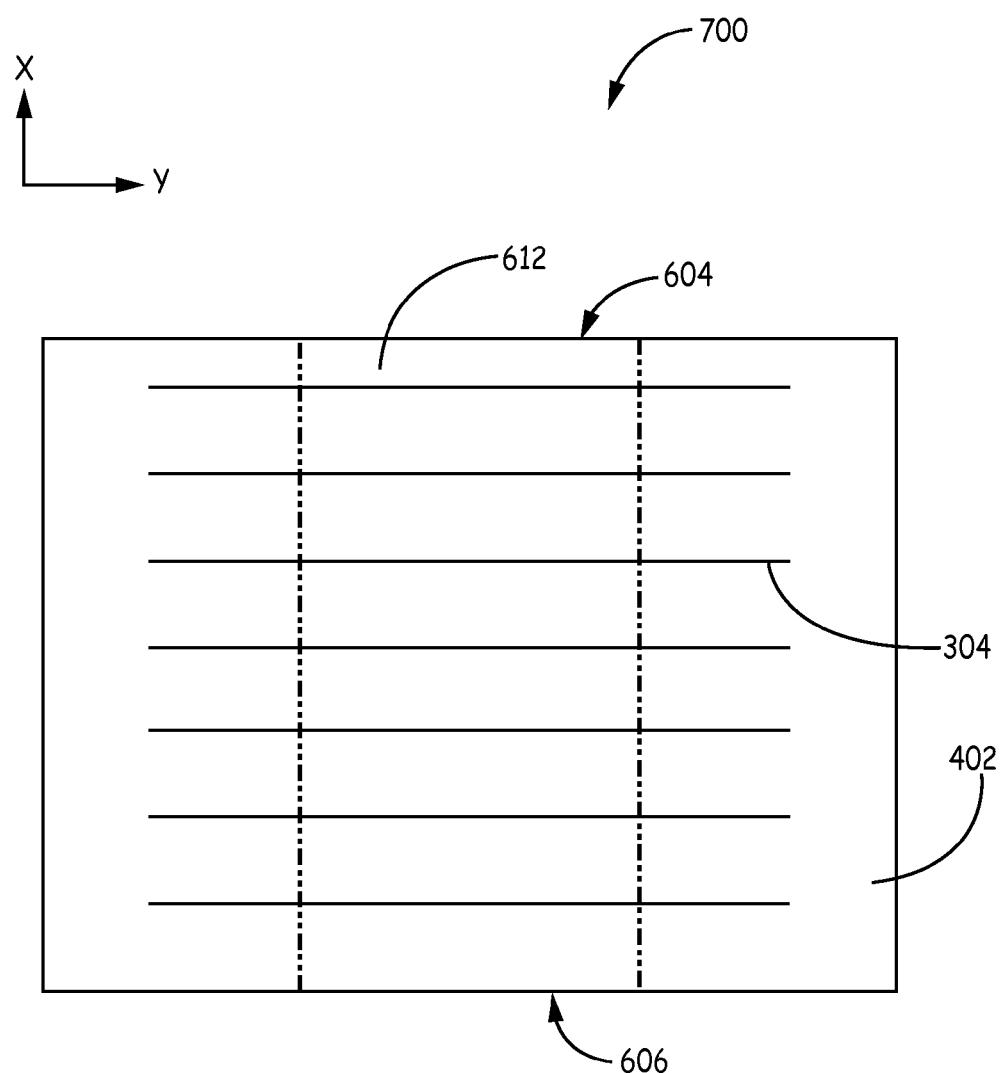
FIG. 7C illustrates a back view of an exemplary non-limiting CCS having a hollow cavity and substantially serpentine-shaped antenna in accordance with embodiments described herein.

As described with reference to FIG. 6, in the embodiment shown, CCS 700 includes completely hollow cavity 612 having open ends 604, 606. FIG. 7B illustrates a front view of an exemplary non-limiting CCS 700 having a hollow cavity 612 and substantially serpentine-shaped antenna 304 in accordance with embodiments described herein. FIG. 7C illustrates a back view of an exemplary non-limiting CCS 700 having a hollow cavity 612 and substantially serpentine-shaped antenna 304 in accordance with embodiments described herein.

Figure 7D:
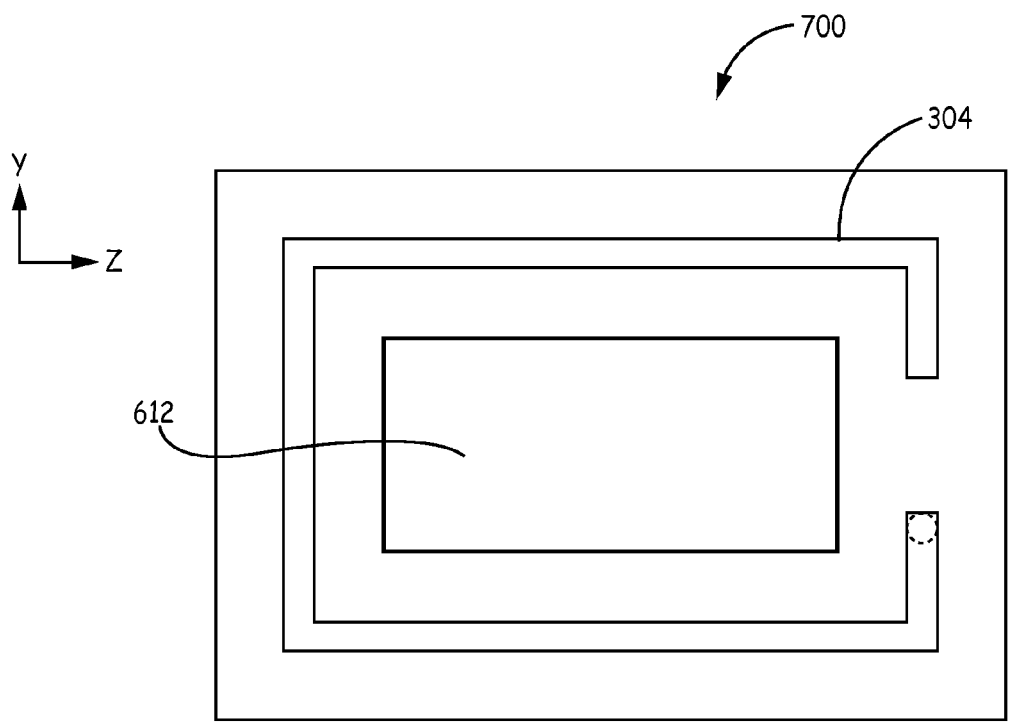
FIG. 7D illustrates a top view of an exemplary non-limiting CCS having a hollow cavity and substantially serpentine-shaped antenna in accordance with embodiments described herein.
Figure 7E:
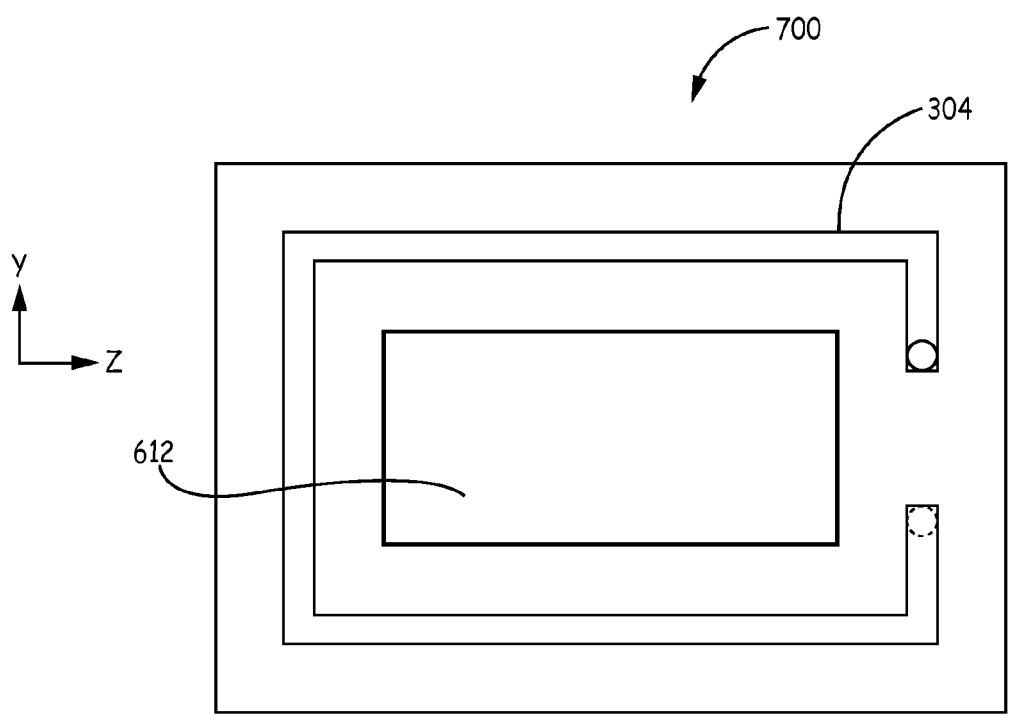
FIG. 7E illustrates a bottom view of an exemplary non-limiting CCS having a hollow cavity and substantially serpentine-shaped antenna in accordance with embodiments described herein.

FIG. 7D illustrates a top view of a top layer of conductive traces of antenna 304 of an exemplary non-limiting CCS 700 having a hollow cavity and substantially serpentine-shaped antenna in accordance with embodiments described herein. As shown, antenna 304 is substantially serpentine-shaped and three-dimensionally placed within wall 402 of CCS 700. In some embodiments, antenna 304 can protrude from a top portion of CCS 700. Hollow cavity 612 is shown with solid line to indicate that end 604 is open and viewable from top view of CCS 700. FIG. 7E illustrates a bottom view of a bottom layer of conductive traces of antenna 304 of an exemplary non-limiting CCS 700 having a hollow cavity and substantially serpentine-shaped antenna in accordance with embodiments described herein. Hollow cavity 612 is shown with solid line to indicate that end 606 is open and viewable from bottom view of CCS 700. As described above, one or more additional layers of dielectric material may reside over the top layer of conductive traces of antenna 304 and/or the bottom layer of conductive traces of antenna 304.

Figure 8A:
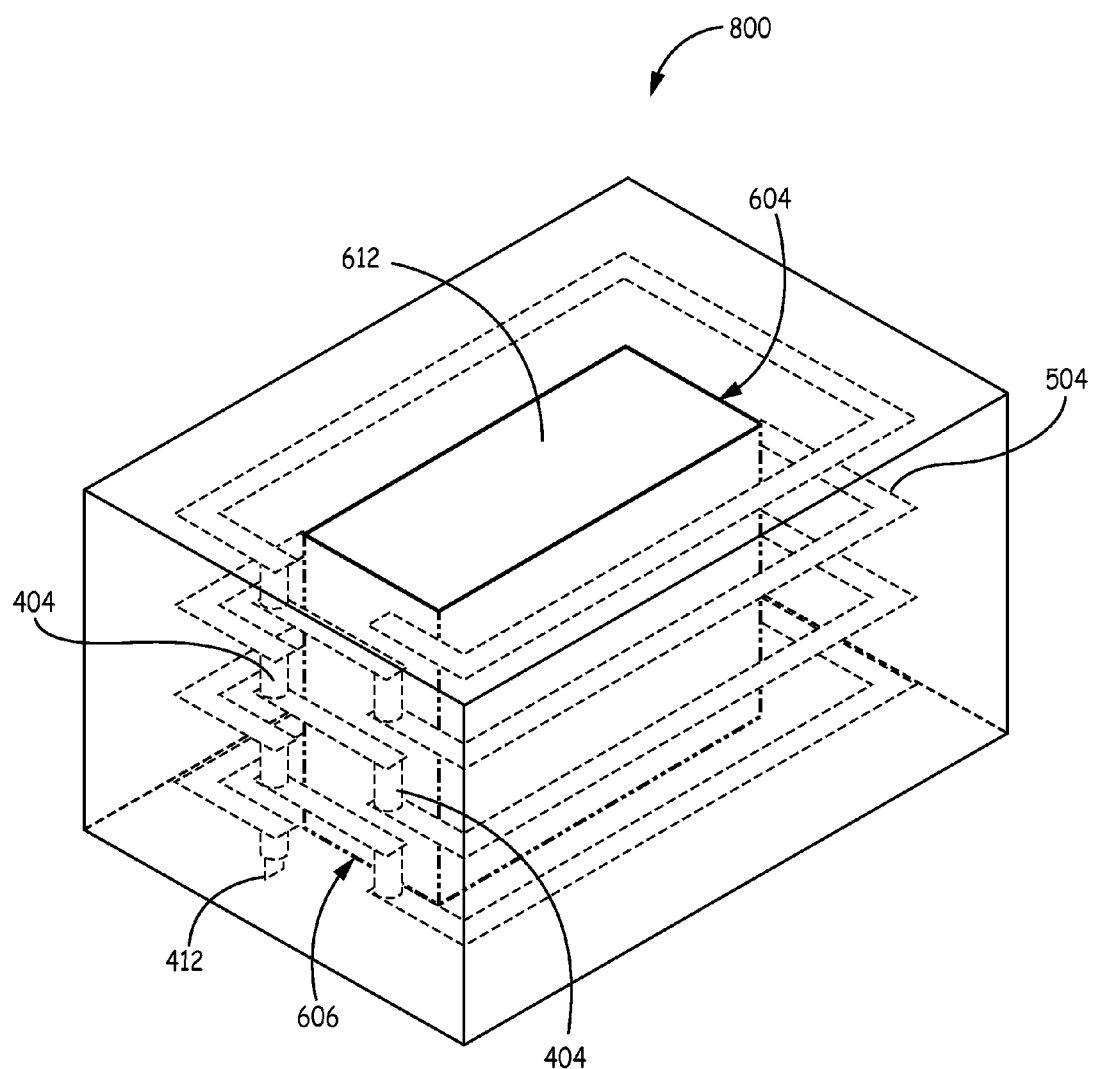
FIG. 8A illustrates a perspective view of an exemplary non-limiting CCS having a hollow cavity and substantially helical-shaped antenna in accordance with embodiments described herein.
Figure 8B:
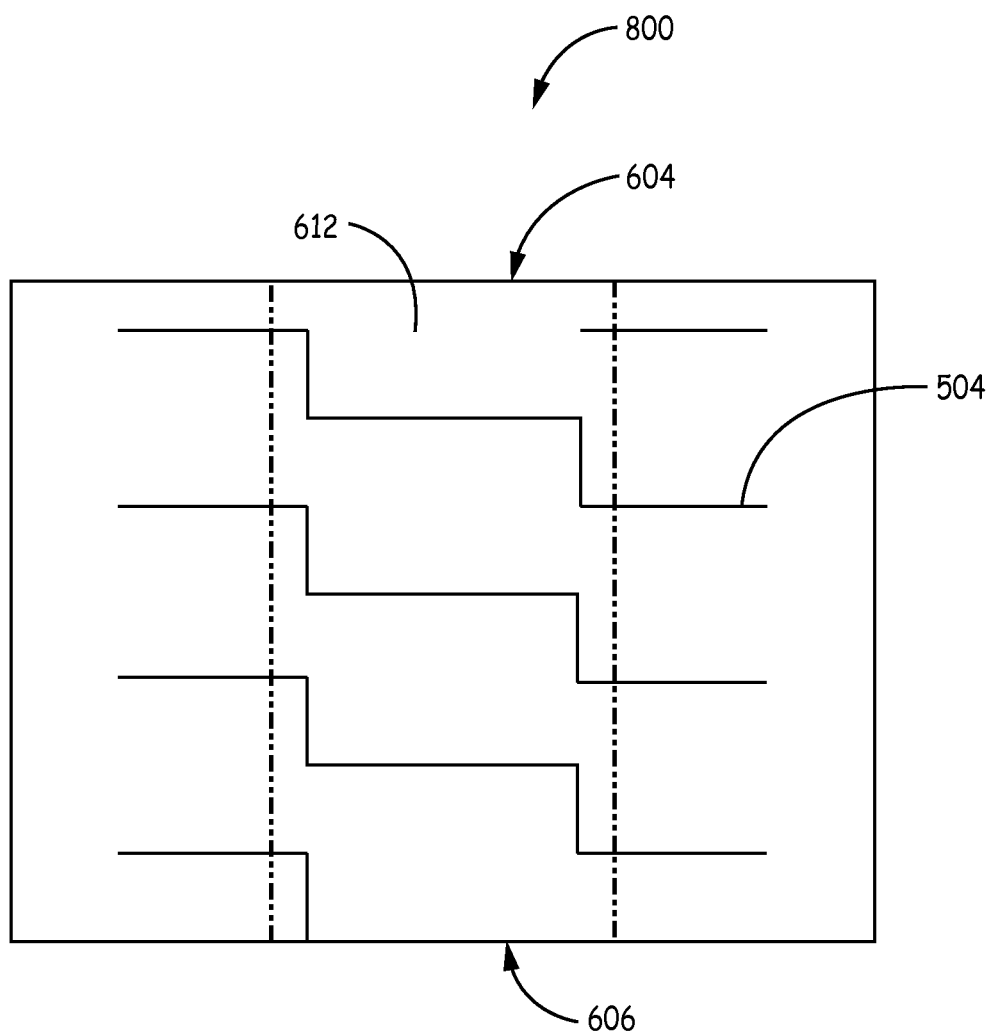
FIG. 8B illustrates a front view of an exemplary non-limiting CCS having a hollow cavity and substantially helical-shaped antenna in accordance with embodiments described herein.
Figure 8C:
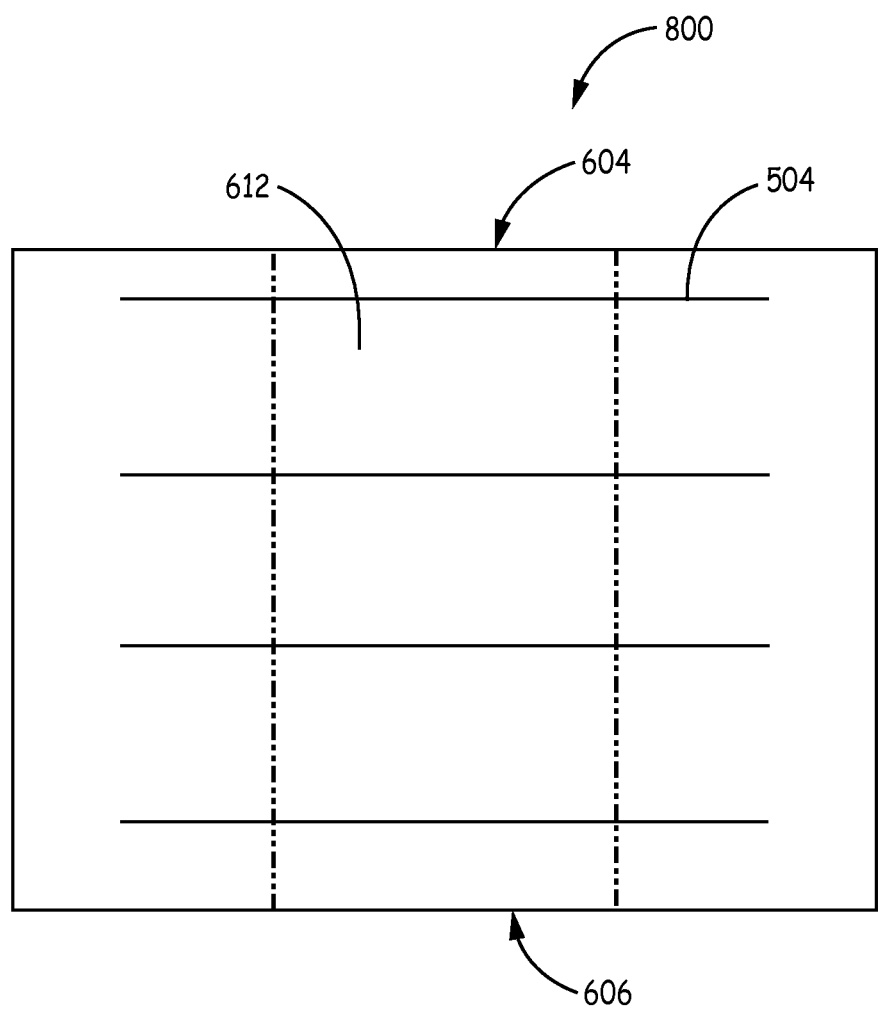
FIG. 8C illustrates a back view of an exemplary non-limiting CCS having a hollow cavity and substantially helical-shaped antenna in accordance with embodiments described herein.
Figure 8D:
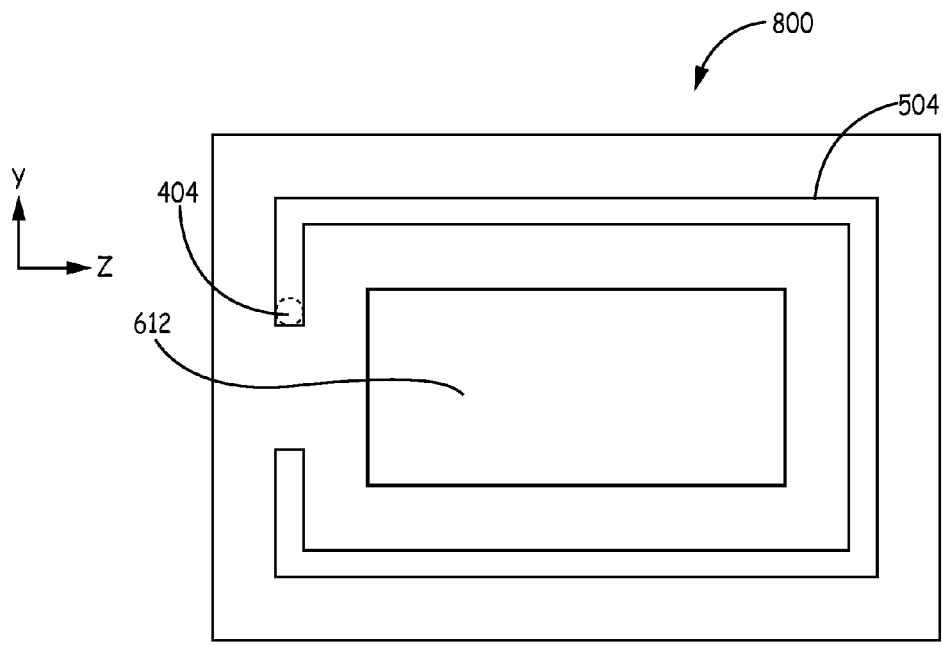
FIG. 8D illustrates a top view of an exemplary non-limiting CCS having a hollow cavity and substantially helical-shaped antenna in accordance with embodiments described herein.
Figure 8E:
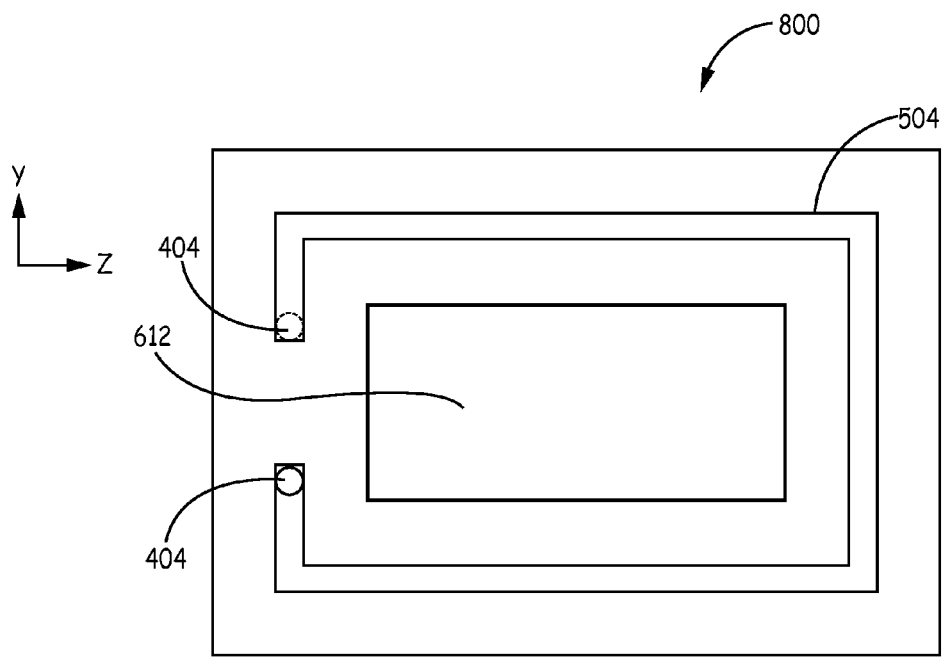
FIG. 8E illustrates a bottom view of an exemplary non-limiting CCS having a hollow cavity and substantially helical-shaped antenna in accordance with embodiments described herein.

FIG. 8A illustrates a perspective view of an exemplary non-limiting CCS having a hollow cavity and substantially helical-shaped antenna 504 in accordance with embodiments described herein. The views of FIGS. 8A, 8B, 8C, 8D and 8E are similar to those of respective FIGS. 7A, 7B, 7C, 7D and 7E albeit antenna 304 is substantially spherical-shaped in FIGS. 7A, 7B, 7C, 7D and 7E while antenna 504 is substantially helical-shaped in FIGS. 8A, 8B, 8C, 8D and 8E. Description of more details of antenna 504 may be found with reference to FIGS. 5A-E.

Figure 9:
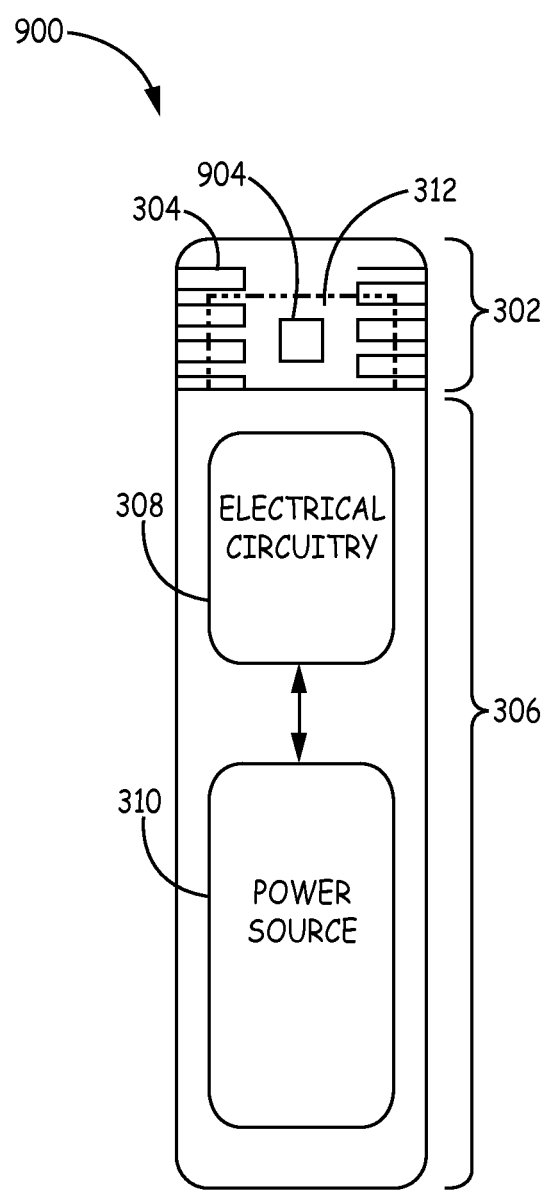
FIG. 9 illustrates a cross-sectional view of an exemplary non-limiting IMD having a cofire-integrated antenna and a cofire-integrated component in accordance with embodiments described herein.

FIG. 9 illustrates a cross-sectional view of an exemplary non-limiting IMD having a CCS 302 having a cofire-integrated antenna 304 and a component 904 within the cavity 612 defined by CCS 302. In various embodiments, IMD 900 can include one or more of the structure and/or functionality of IMD 102, 200, 300, 600 (and vice versa). Repetitive description of like elements employed in other embodiments is omitted for sake of brevity.

As shown, IMD 900 can include CCS 902 having cofire-integrated three-dimensional antenna 304 embedded in CCS 902, component 904 within hollow cavity 312, and housing 306. In some embodiments, housing 306 can have an open end adjacent the open end of cavity CCS 302 and component 904 can extend through the open end into hollow cavity 312 of CCS 302. Electrical circuitry 308 may, for example, include a hybrid integrated circuit or multi-chip module having a number of components such as integrated circuit, active components, or passive components on a printed circuit board (PCB) or other substrate. The substrate may be formed such that a portion of the substrate fit within the hollow cavity 312 of CCS 902. As such, component(s) 904 would include the components on the portion of the substrate that fits within the hollow cavity 312 of CCS 902. Alternatively, the battery or other power source may be placed partially within cavity 312 of CCS 302.

IMD 900 can also include electrical circuitry 308 and/or power source 310 configured to power IMD 900 (or one or more components of IMD 900). In various embodiments, one or more of CCS 902 having cofire-integrated antenna 304 embedded in CCS 902, component 904, housing 306, electrical circuitry 308 and/or power source 310 can be communicatively and/or electrically coupled to one another to perform one or more functions of IMD 900.

In various embodiments, component 904 can include any number of different types of components configured to perform an electrical function, such as one of the components described above with respect to FIG. 3 as being part of electrical circuitry 308. For example, component 904 can be a telemetry module (e.g., transmitter, receiver, transceiver or RF chip) disposed in hollow cavity 312 and electrically or conductively coupled to antenna 304. Although not shown, in some embodiments, to accommodate the structure shown, feedpoint 412 is located at the wall of hollow cavity 312. In another example, component 904 can include one or more passive elements (e.g., capacitors and/or inductors) or an entire impedance matching network for antenna 304 disposed in hollow cavity 312 and electrically or conductively coupled to antenna 304. The impedance matching network can modify the impedance of antenna 304 to desired levels, for example. In other embodiments, component 904 can be or include one or more sensing electrodes. The sensing electrode, capacitor, inductor, RF chip, IC and/or any components described herein can be provided in hollow cavity 312 in CCS 902.

While the embodiment of FIG. 9 illustrates and describes a substantially serpentine-shaped configuration of antenna 304, in different embodiments, any number of other configurations of antennas can be employed, including the helical-shaped antenna 504. Additionally, although illustrated in the context of a cap-shaped CCS, component 904 may be located within the hollow cavity 612 of any of the sleeve CCSs described above. Further, as noted, in various embodiments, any number of different types of components that perform electrical functions can be employed in the embodiments shown and described.

Figure 10A:
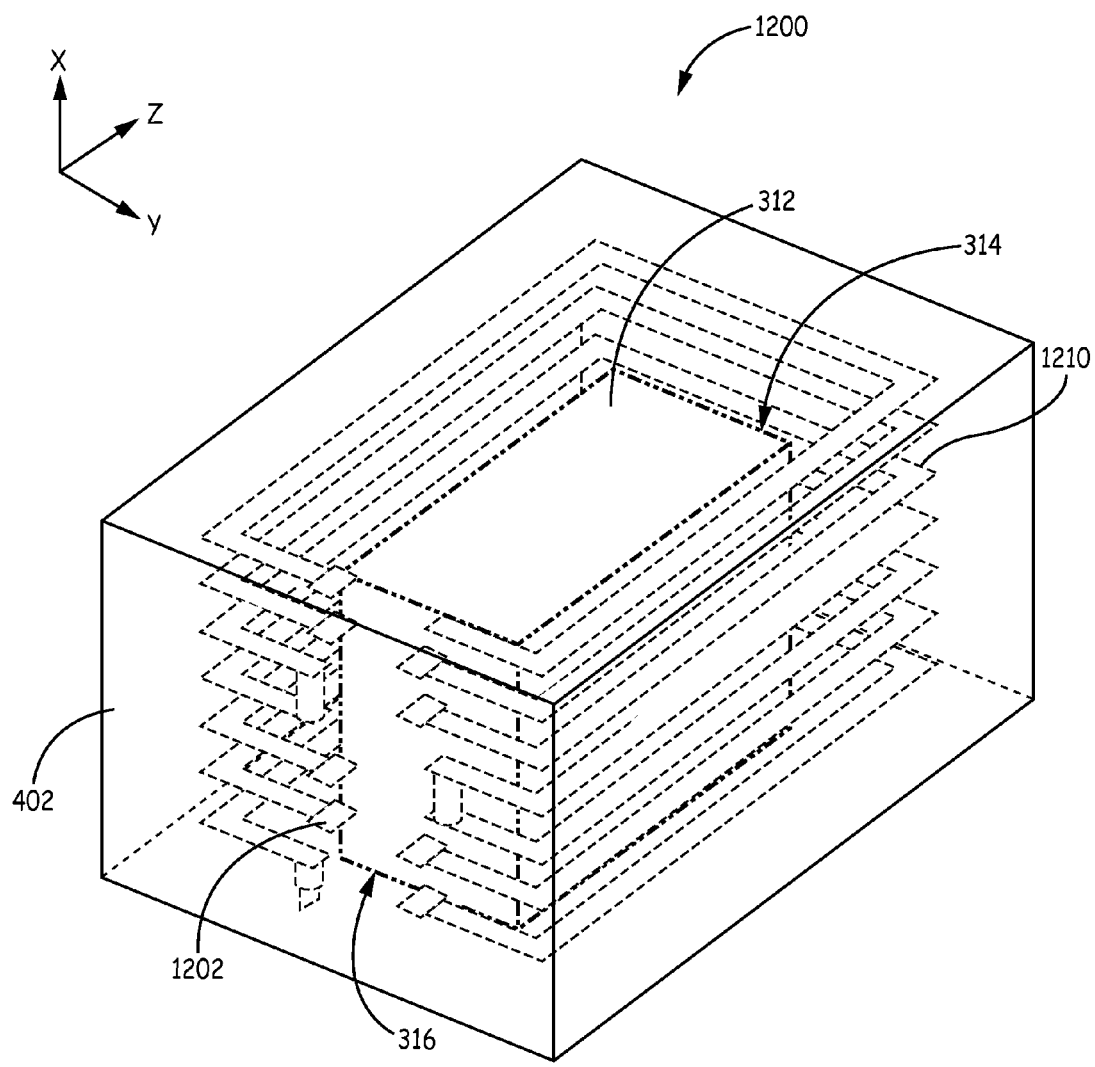
FIG. 10A illustrates a perspective view of an exemplary non-limiting CCS having a partially hollow cavity and antenna with capacitive interconnections in accordance with embodiments described herein.
Figure 10B:
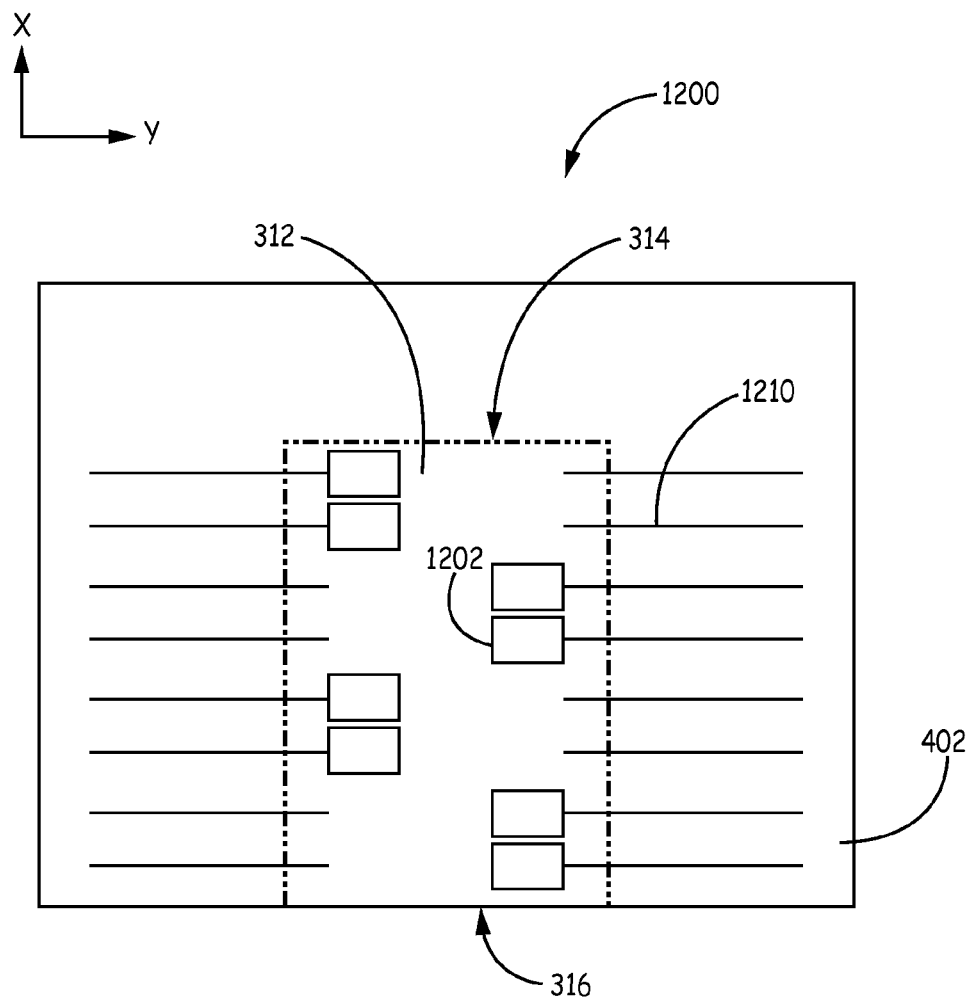
FIG. 10B illustrates a front view of an exemplary non-limiting CCS having a partially hollow cavity and antenna with capacitive interconnections in accordance with embodiments described herein.
Figure 10C:
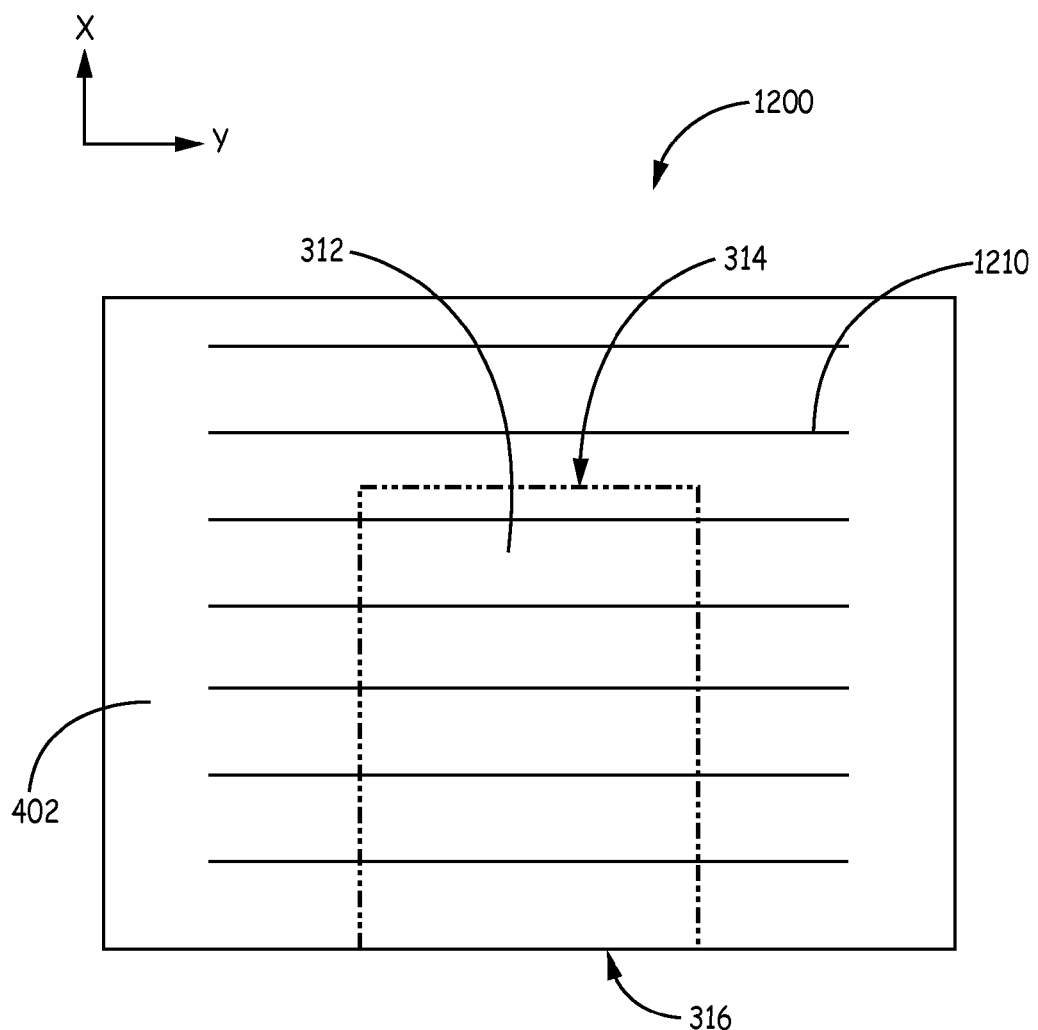
FIG. 10C illustrates a back view of an exemplary non-limiting CCS having a partially hollow cavity and antenna with capacitive interconnections in accordance with embodiments described herein.
Figure 10D:
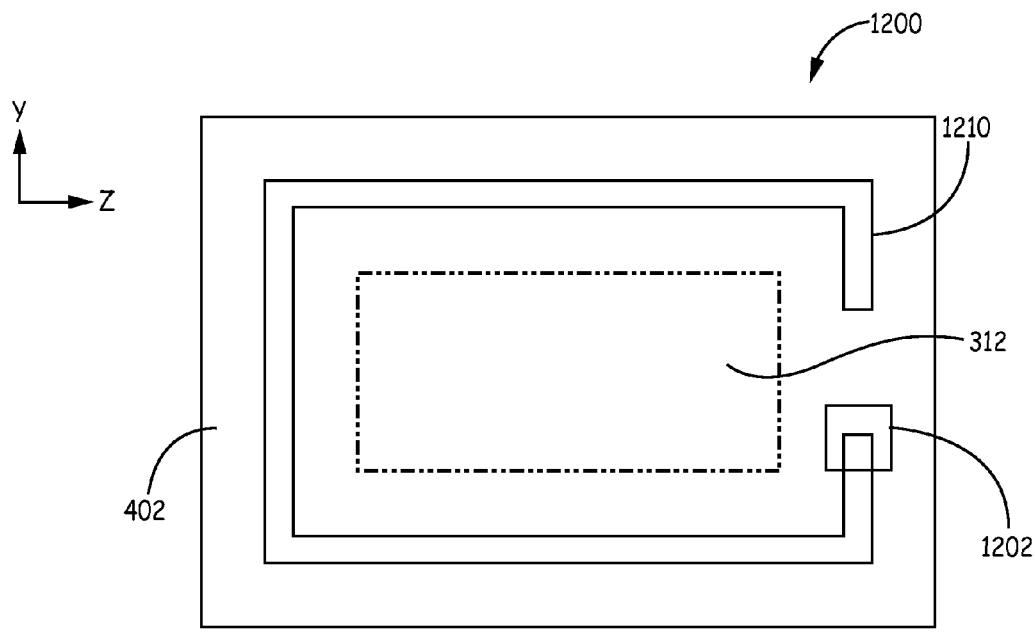
FIG. 10D illustrates a top view of an exemplary non-limiting CCS having a partially hollow cavity and antenna with capacitive interconnections in accordance with embodiments described herein.
Figure 10E:
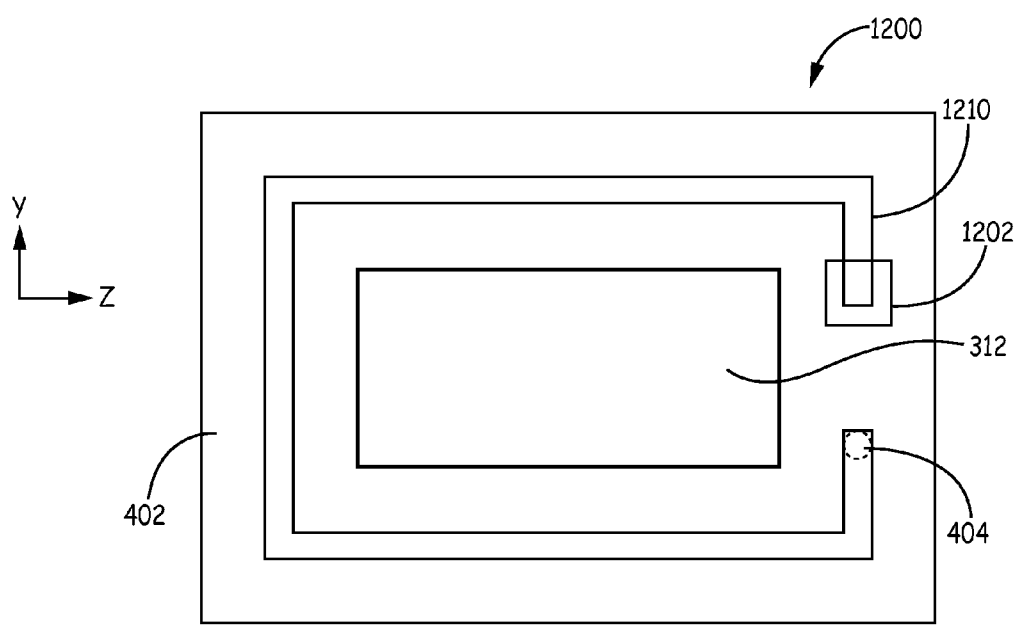
FIG. 10E illustrates a bottom view of an exemplary non-limiting CCS having a partially hollow cavity and antenna with capacitive interconnections in accordance with embodiments described herein.

FIG. 10A illustrates a perspective view of an exemplary non-limiting CCS 1200 having a partially hollow cavity and antenna with capacitive interconnections in accordance with embodiments described herein. In various embodiments, CCS 1200 can include one or more of the structure and/or functionality of CCS 302, 400, 500, 602, 700, 800, 902 and 1000 (and vice versa). Repetitive description of like elements employed in other embodiments is omitted for sake of brevity.

Shown is CCS 1200 having hollow cavity 312, three-dimensional antenna 1210 and capacitive interconnections in accordance with one or more embodiments described herein.

In lieu of providing apertures for vias on dielectric layers that, when cofired, form CCS 1200 having vias 404 between portions of conductive traces of the antenna, material can be deposited on the dielectric layers for forming metal pads or plates 1202 on the ends of the conductive traces that are substantially parallel with one another. As such, metal pads or plates 1202 are separated from one another by dielectric forming a capacitive structure. In this manner, the signals are capacitively coupled from the metal pad on one layer (e.g., pads 1202) to the metal pad on the subsequent layer to capacitively couple the signal through the various portions of antenna 1210.

Upon cofiring, the capacitive interconnections can form between the portions of antenna 1210. In some embodiments, the capacitive interconnections can be substantially parallel capacitive interconnections. Numerous capacitive interconnections can be formed on a dielectric layer based on the desired conductivity across antenna 1210 and/or CCS 1200 after cofiring. For ease of illustration, however, FIG. 10A illustrates only four capacitive interconnections. However, capacitive interconnections can be formed at each portion of antenna 1210 in which via interconnections were provided in antenna 304 of FIGS. 4A-4E, for example, or in antenna 504 illustrated in FIGS. 5A-5E. In other embodiments, the portions of conductive traces on different layers may be connected using a combination of vias and capacitive interconnections, e.g., some portions connected using vias and other portions connected using metal pads or plates for forming capacitive interconnections.

Capacitive interconnections can be provided along a first axis of CCS 1200 formed after cofiring by placing the material for the substantially capacitive interconnections in substantially same locations on the different dielectric layers. In some embodiments, after cofiring, capacitive interconnections in CCS 1200 can be conductively coupled to a metal pad (not shown) or feedpoint (e.g., feedpoint 412) external to, or in an exterior surface of, CCS 1200. The metal pad or feedpoint can be electrically coupled to electrical circuitry 308 in a housing of an IMD, for example.

While the embodiments of FIGS. 10A-12E detail one particular configuration of antenna 1210, in various embodiments, any number of configurations of antenna 1210 can be employed with cofire-integrated capacitive interconnections, including helical-shaped antenna 504.

There are several advantages to employing cofire-integrated capacitive interconnections in lieu of vias including, but not limited to, simplified design and manufacturing process, and added electromagnetic filtering functionality. The embodiments incorporating capacitive coupling can reduce or eliminate the need for vias in adjacent layers so the overall design may be simpler and cheaper. Further, by adjusting the size of the surface metal pads the capacitance can be tailored to filter out, or reduce the amount of, unwanted parasitic electromagnetic signals relative to embodiments having through hole via interconnections. Additionally, these configurations can provide the antenna with better impedance matching.

Figure 11:
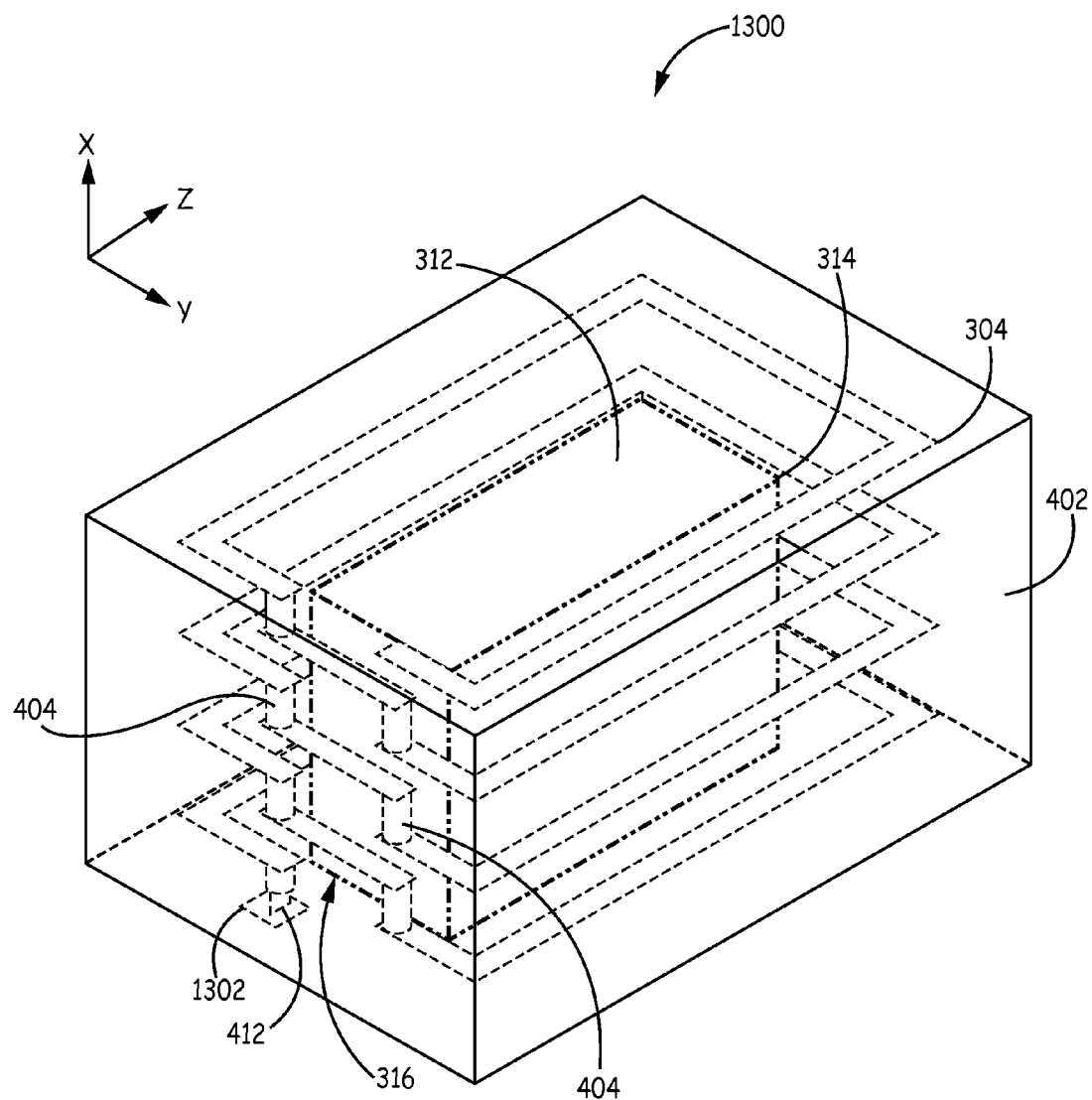
FIG. 11 illustrates a perspective view of an exemplary non-limiting CCS having a partially hollow cavity with cofire-integrated antenna and metal pad in accordance with embodiments described herein.

FIG. 11 illustrates a perspective view of an exemplary non-limiting CCS 1300 having a partially hollow cavity 312 with cofire-integrated antenna 304 and metal pad 1302 in accordance with embodiments described herein. In some embodiments, metal pad 1302 can be provided on an exterior surface of CCS 1300. Metal pad 1302 can cofire-integrated into CCS 1300 such that it is exposed on an exterior surface of CCS 1300. For example, prior to cofiring, conductive material from which the metal pad is composed can be provided on a side of at least one dielectric layer that will be an external surface of CCS 1300 after cofiring. The conductive material can be deposited via screen printing, for example. After cofiring, metal pad 1302 can enable conductivity between antenna 304 and a component (not shown) in a housing of an IMD.

In various embodiments, metal pad 1302 is formed in different configurations and/or sizes. Further, whether metal pad 1302 is electrically coupled to antenna 304 and/or the size of metal pad 1302, can be a design choice based on the size of CCS 1300, access to antenna 304, the interconnect method between metal pad 1302, and a feedthrough and/or any number of other considerations. Regardless, the use of a metal pad 1302 as a feedpoint may eliminate the need for more complicated feedthroughs to couple the antenna to the transmitter, receiver or transceiver of the ICD.

Further, the interconnect method between metal pad 1302 and a feedthrough or other feedpoint of the IMD can be at least partially dictated by whether a biocompatible metal pad is desired. For example, if CCS 1300 is located outside of a hermetically sealed housing, a biocompatible and biostable metal pad is desired. The interconnection method can be one that can provide a biocompatible connection between metal pad 1302 and CCS 1300 that is not likely to corrode over time (e.g., welding).

Welding can be employed in conjunction with metals that are stable in aqueous/body fluid environments, for example. Examples of such metals include, but are not limited to, niobium, platinum, stainless steels and titanium.

Any number of welding techniques can be employed to form hermetic joints between metal pad 1302 and a feedthrough, for example. Welding techniques for providing a biocompatible and biostable include, but are not limited to, those using heat sources, such as parallel gap welding, laser welding or otherwise joining with a laser (e.g., laser brazing, laser soldering, laser chemical reaction, laser softening of glue), opposed gap welding, step gap welding, diffusion bonding (pressure and temperature), braze or solder in a furnace, braze or solder with resistance heating, braze or solder with a laser, ultrasonic bonding, weld/ball/ribbon welding, reaction welding, sintering, and exothermic reaction of a multilayer stack. Mechanical joining techniques for establishing an electrical contact can include scraping, pressure contact, and pin and socket.

In some embodiments, an interposer (e.g., a platinum pad of a cofire feedthrough pad or pad array) can be joined to the feedthrough. In various embodiments, the interposer can be, but is not limited to, thin film, thick film, blocks, lead frames, stack of cofire components joined with gold braze or platinum-sintered cofire pads (or of other alloys such as platinum-iridium or other nano-sized particles of refractory biostable, biocompatible metals such as platinum, titanium, tantalum, niobium, gold, and alloys and oxides thereof).

In some embodiments, a conductive lead (e.g., platinum, platinum-iridium alloy, titanium, tantalum, niobium, gold, and alloys and oxides thereof) can be subsequently welded to the interposer using a variety of joining techniques to form a hermetic joint of the interposer to a feedthrough. Joining techniques for providing a biocompatible and biostable joint include, but are not limited to, those using heat sources, diffusion bonding (pressure and temperature), brazing or soldering in a furnace, brazing or soldering with resistance heating, brazing or soldering with a laser or otherwise joining with a laser, ultrasonic bonding, reaction welding, and exothermic reaction of a multilayer stack. In some embodiments, hybrid approaches that combine joining techniques can be used to form a hermetic joint of a lead to a feedthrough.

In some embodiments, parallel gap welding of a lead formed from an alloy (e.g., alloy including nickel, cobalt, and chromium) to a platinum pad can be conducted without damaging hermeticity of the joint between the metal pad and the feedthrough by using a current of less than 0.5 kiloamperes (kA) (e.g., about 0.13 kA), a force of less than five pounds per electrode (e.g., about 2 lb. force/electrode), using copper-based metal matrix composite alloy electrodes (e.g., sized about 0.015 by about 0.025 inch), and in an inert cover gas (e.g., argon, helium, nitrogen, etc.).

The thickness of metal pad 1302 on CCS 1300 can be at least about 3 mils to provide adequate thermal isolation of the underlying brittle ceramic from the input weld energy. The planar size of metal pad 1302 will be designed to provide adequate space for the appropriate interconnect method. Further, antenna 304 and/or metal pad 1302 can be composed of biocompatible material such as niobium. Finally, a feedthrough can be a traditional feedthrough in this embodiment and include a pin or ribbon making up the feedthrough.

In embodiments in which CCS 1300 and metal pad 1302 are located within a hermetically sealed housing of the IMD, the interconnect method between metal pad 1302 and CCS 1300 need not be biocompatible. In particular, metal pad 1302 can be formed after CCS 1300 is cofired or used in its cofire condition (without further welding, for example). In this case, metal pad 1302 can be a thinner platinum pad similar in structure to a surface mount soldered interconnect and can be placed on a newly-machined exterior surface of CCS 1300. The thinner platinum pad can have thin film metal layers that enable the use of common solder materials and processes. In some embodiments, metal pad 1302 can be cofired within CCS 1300.

Accordingly, in embodiments in which metal pad 1302 will not be exposed to bodily fluid or gases, the interconnect method can be any of the traditional approaches (which would tend to corrode over time if exposed to wet environments such as those inside of a human body. These interconnect methods can include, but are not limited to, surface mount methods, solder methods or wire bonding.

Figure 12A:
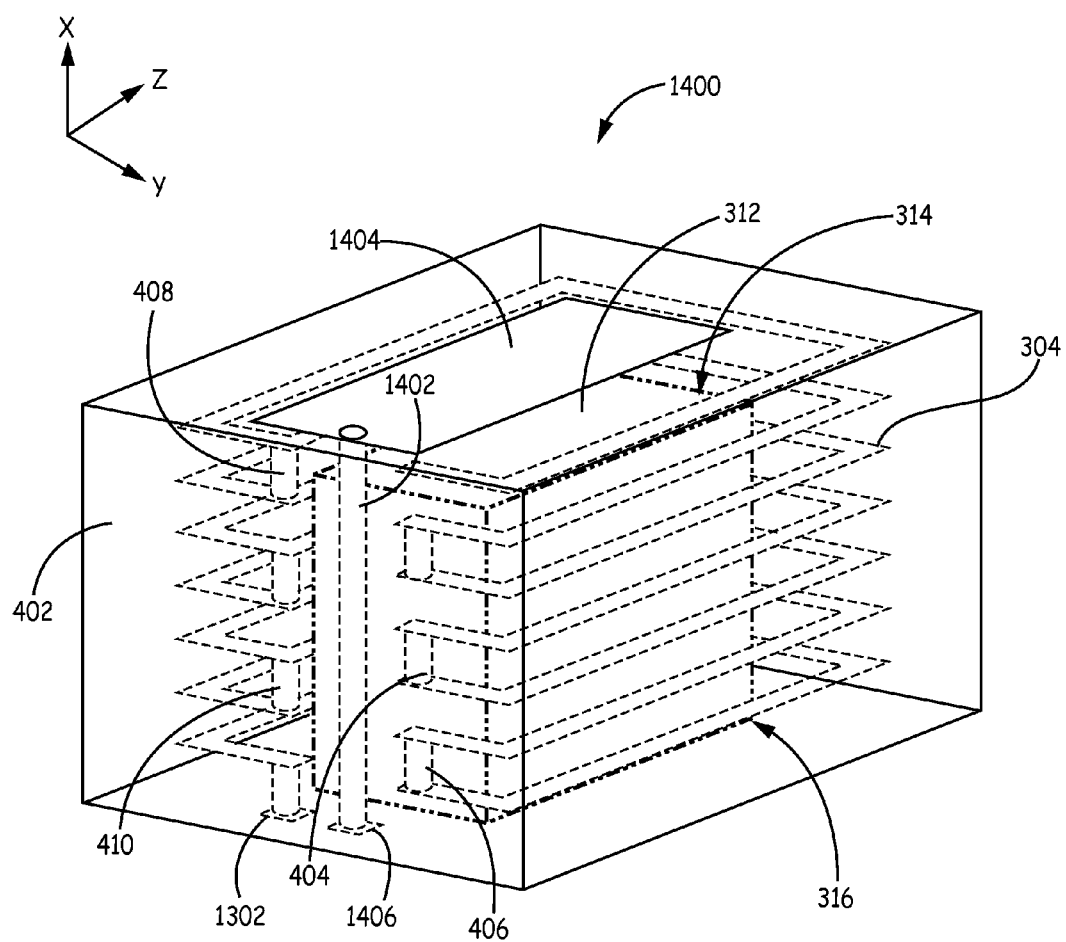
FIG. 12A illustrates a perspective view of an exemplary non-limiting CCS having a partially hollow cavity with cofire-integrated antenna, feedthrough and electrode in accordance with embodiments described herein.

FIG. 12A illustrates a perspective view of an exemplary non-limiting CCS 1400 having a partially hollow cavity 312 with cofire-integrated antenna, feedthrough and metal pads in accordance with embodiments described herein. In various embodiments, CCS 1400 can include one or more of the structure and/or functionality of CCS 302, 400, 500, 602, 700, 800, 902, 1000 (and vice versa). Further, repetitive description of like elements employed in other embodiments is omitted for sake of brevity.

In various embodiments, one or more different components can be cofire-integrated into the wall of CCS 1400 or provided in hollow cavity 312 of CCS 1400. The components can be any number of different components that can perform one or more electrical functions and/or output one or more electrical signals. By way of example, but not limitation, the component can be a feedthrough, sensing electrode, integrated circuit, passive network (or component thereof) or the like. Shown in FIG. 12A is feedthrough 1402 electrically and/or conductively coupling an electrode 1404 to a contact pad 1406. Electrode 1404 may, in some instances, be directly exposed to bodily tissue and/or fluids when the IMD including CCS 1400 is implanted. In other instances, electrode 1404 may include at least one dielectric layer separating electrode 1404 from directly contacting bodily tissue and/or fluid, but electrode 1404 may still be capable of sensing electrical signals of the heart of the patient in which the IMD including CCS 1400 is implanted. In various embodiments, material from which feedthrough 1402 is composed can be provided in or on one or more of the dielectric layer to form feedpoint 1402 upon cofiring.

Figure 12B:
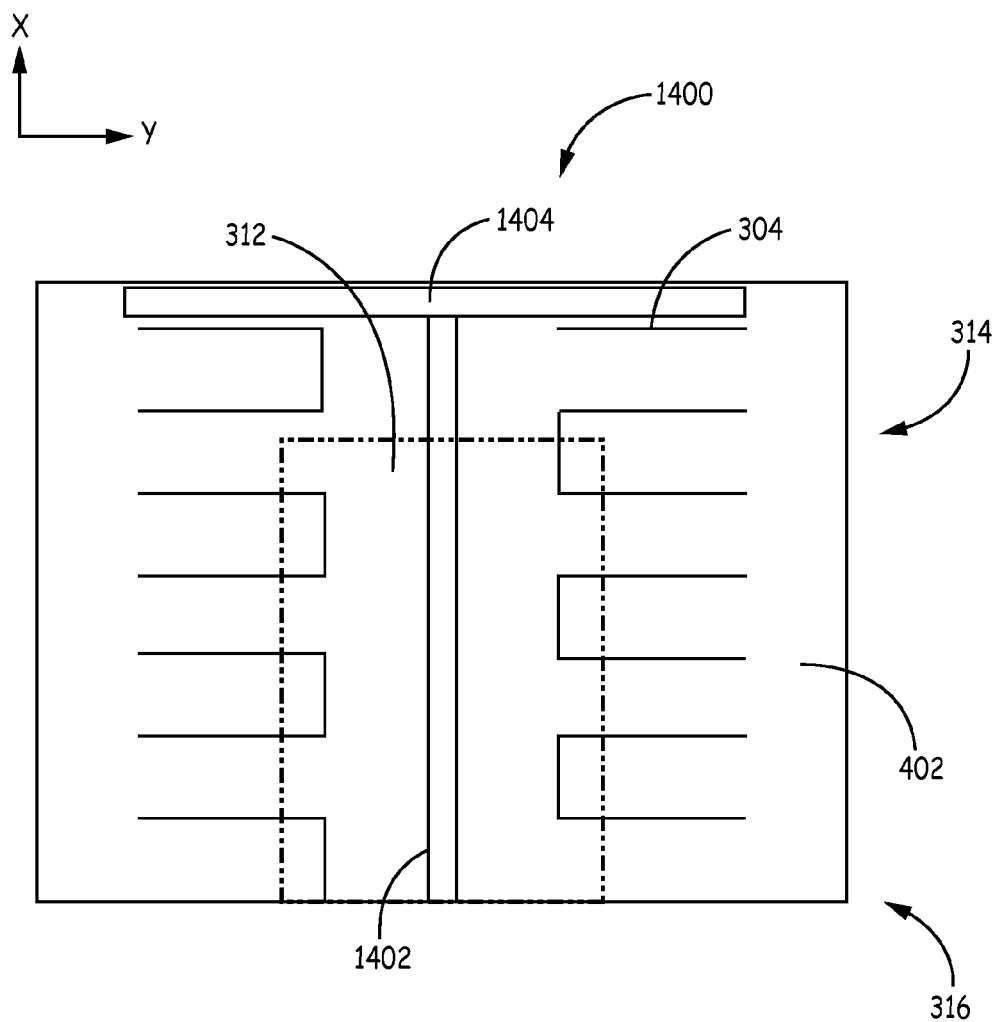
FIG. 12B illustrates a front view of an exemplary non-limiting CCS having a partially hollow cavity with cofire-integrated antenna, feedthrough and electrode in accordance with embodiments described herein.
Figure 12C:
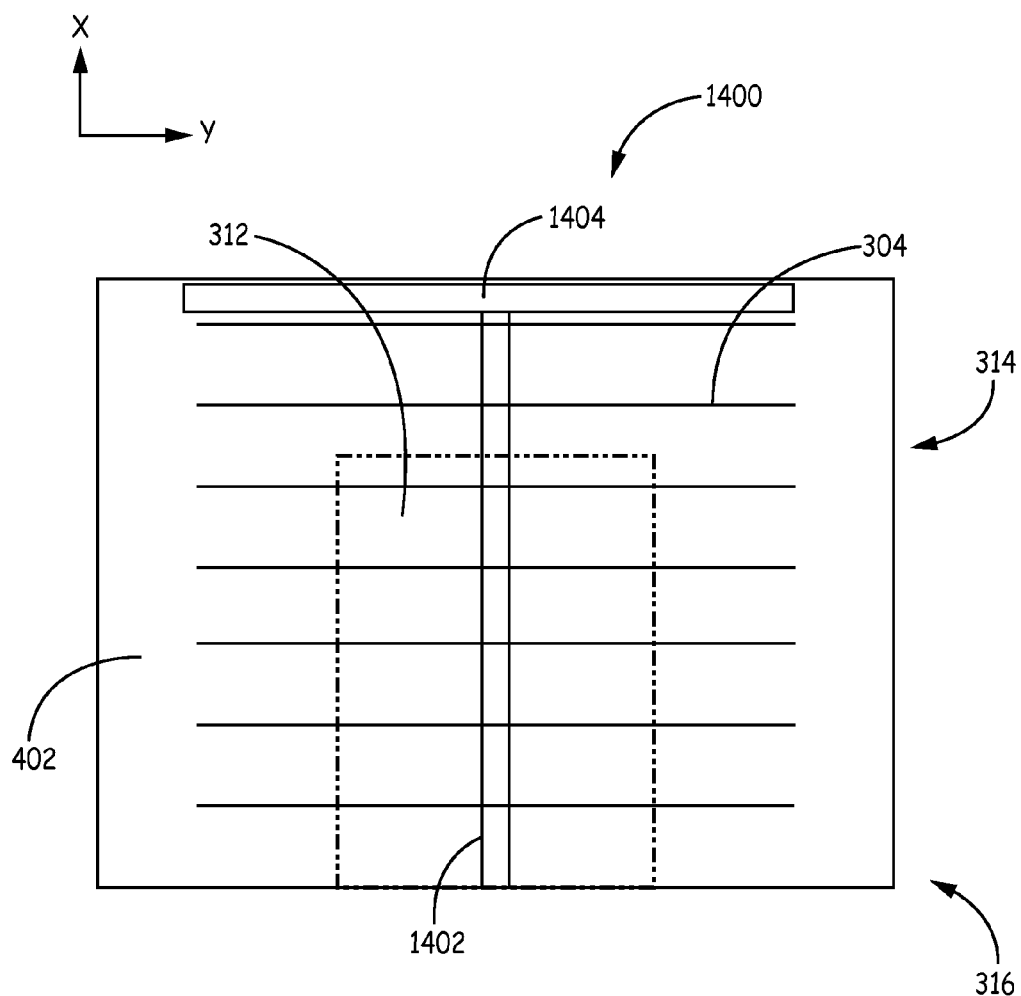
FIG. 12C illustrates a back view of an exemplary non-limiting CCS having a partially hollow cavity with cofire-integrated antenna, feedthrough and electrode in accordance with embodiments described herein.
Figure 12D:
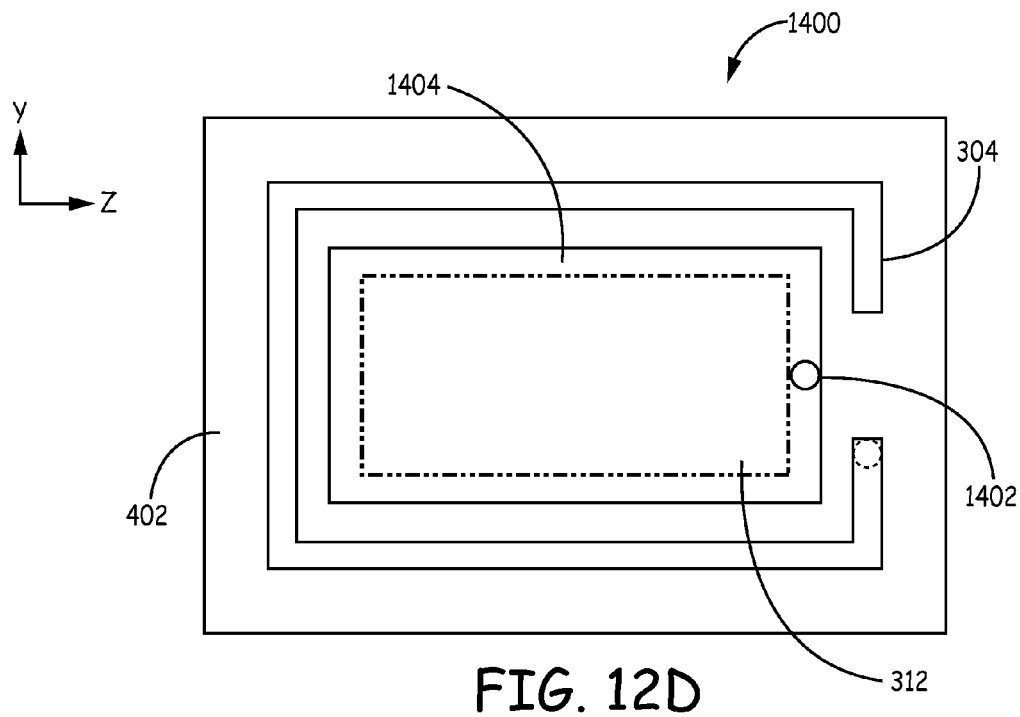
FIG. 12D illustrates a top view of an exemplary non-limiting CCS having a partially hollow cavity with cofire-integrated antenna, feedthrough and electrode in accordance with embodiments described herein.
Figure 12E:
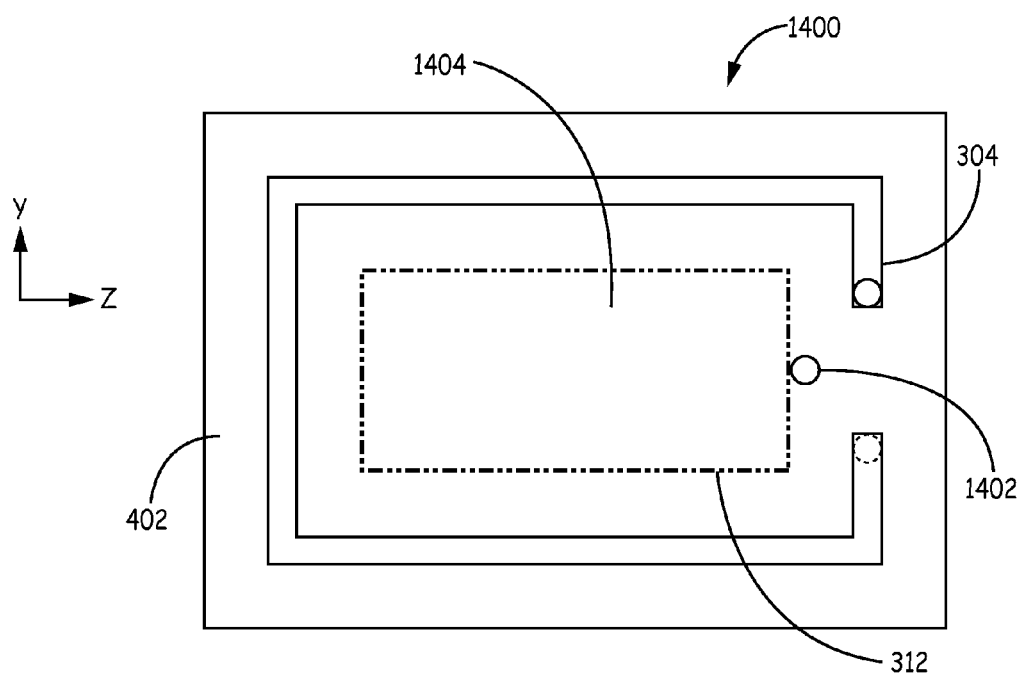
FIG. 12E illustrates a bottom view of an exemplary non-limiting CCS having a partially hollow cavity with cofire-integrated antenna, feedthrough and electrode in accordance with embodiments described herein.

FIG. 12B illustrates a front view of an exemplary non-limiting CCS having a partially hollow cavity with cofire-integrated antenna, feedthrough and metal pads in accordance with embodiments described herein. FIG. 12C illustrates a back view of an exemplary non-limiting CCS having a partially hollow cavity with cofire-integrated antenna, feedthrough and metal pads in accordance with embodiments described herein. FIG. 12D illustrates a top view of an exemplary non-limiting CCS having a partially hollow cavity with cofire-integrated antenna, feedthrough and metal pads in accordance with embodiments described herein. FIG. 12E illustrates a bottom view of an exemplary non-limiting CCS having a partially hollow cavity with cofire-integrated antenna, feedthrough and metal pads in accordance with embodiments described herein.

Figure 13:
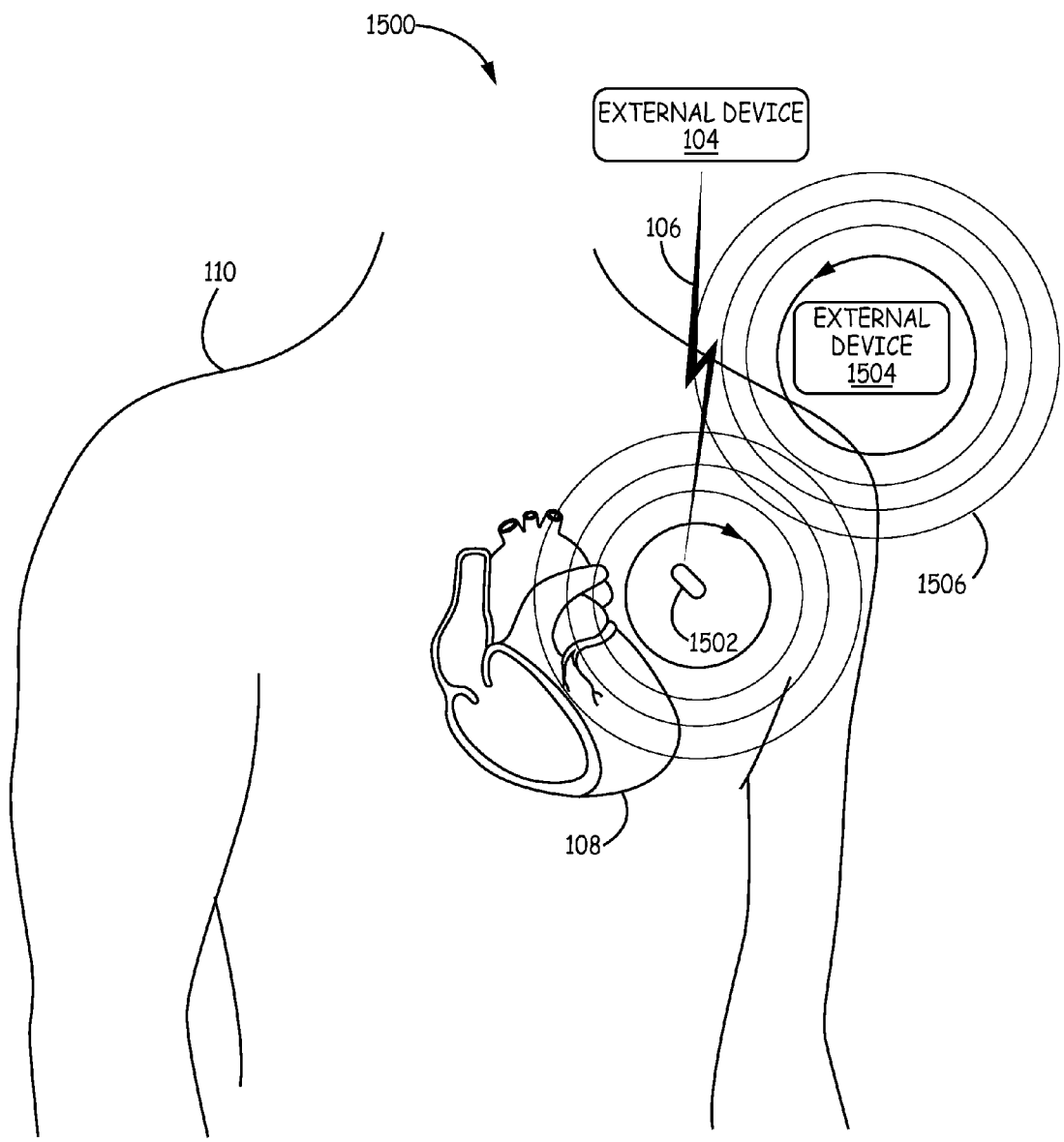
FIG. 13 illustrates a schematic diagram of an exemplary non-limiting medical device telemetry system including an external device and an IMD with CCS having cofire-integrated antenna in accordance with one or more embodiments described herein.
Figure 14:
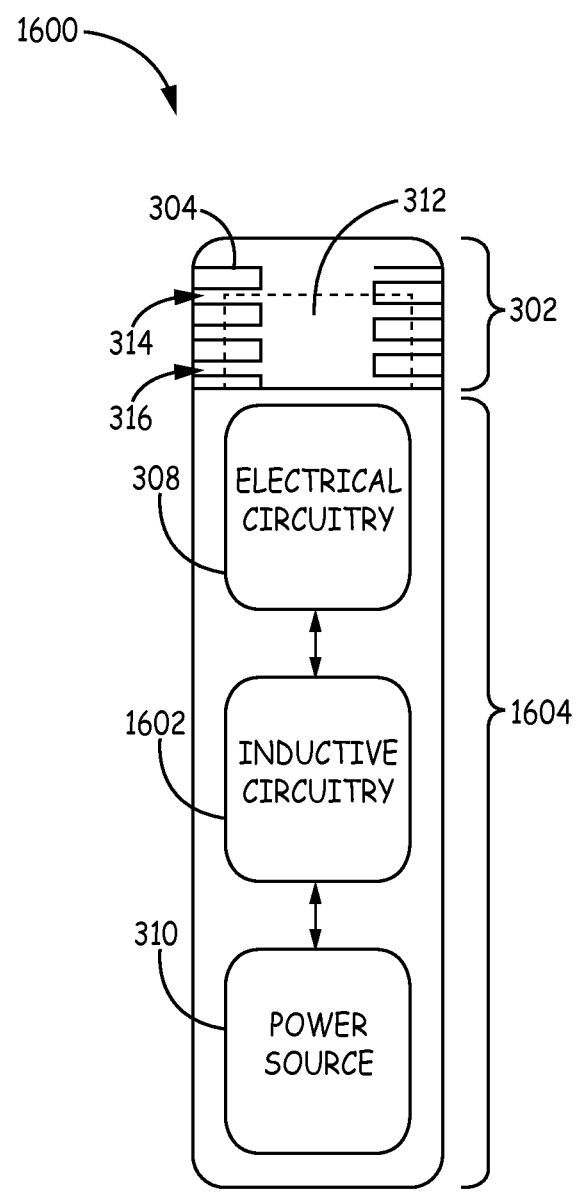
FIG. 14 illustrates a cross-sectional view of an exemplary non-limiting IMD having a CCS in accordance with embodiments described herein.

FIG. 13 illustrates a schematic diagram of an exemplary non-limiting medical device telemetry system including an external device and an IMD with CCS having cofire-integrated antenna in accordance with one or more embodiments described herein. FIG. 14 illustrates a cross-sectional view of an exemplary non-limiting IMD having a CCS in accordance with embodiments described herein. Repetitive description of like elements employed in other embodiments is omitted for sake of brevity.

Turning to FIG. 13, medical device telemetry system 1500 includes IMD 1502 and external device 104 communicatively coupleable to IMD 1502 via wireless channel 106 and external device 1504 inductively coupleable to IMD 1502 via magnetic field 1506. IMD 1502 can perform any number of functions for detection and/or treatment of medical conditions, including, but not limited to, those described with reference to IMD 102, 200, 300, 600, 900. In various embodiments, one or more of the structure and/or function of IMD 1502 can be as described for IMD 1600 of FIG. 14 (and vice versa).

Turning now to FIG. 14, as shown, IMD 1600 can include CCS 302 coupled to housing 1604, and housing 1604 can include inductive circuitry 1602. Inductive circuitry 1602 can include a circuit having a primary coil with a defined number of turns dictated by the desired strength of the magnetic field to be generated by the primary coil. In various embodiments, although not shown, inductive circuitry 1602 can be electrically coupled to power source 310 to provide for charging/re-charging power source 310, for example. External device 1504 can include a secondary coil that can be brought into close proximity (e.g., 2-10 centimeters) of IMD 1502 (and inductive circuitry 1602) to cause a magnetic field to generate between external device 1504 and IMD 1502. Current flowing through the inductive circuitry 1602 can be employed to charge/re-charge power source 310 in some embodiments, for inductive coupling communication in other embodiments or the like.

The material of housing 1604 can differ depending on the operation of IMD 1502. For example, for operation at lower frequencies (e.g., below 1 megahertz (MHz)), housing 306 can be composed of metal and inductive coupling circuitry 1602 can be located inside of housing 306. However, for operation at higher frequencies (e.g., 13.56 MHz), inductive circuitry 1602 can be located within a plastic structure (e.g., housing 306 composed of plastic and/or the CCS of IMD 1600.

Tissue conductance communication protocols, which measure a potential difference between tissues at two points in the body across which a current has been transmitted, can also be employed.

In various embodiments, one or more of the CCSs described herein can be generated according to a cofire ceramic fabrication process that can advantageously facilitate size reduction of antennas and RF transparent structures employed in IMDs thereby increasing the potential for widespread medical device telemetry systems.

A non-limiting exemplary process for generating one or more of the CCSs described herein can include one or more of the following steps. One or more layers of dielectric are independently processed, and the layers are subsequently collated and laminated to one another. The laminated structure can then be cut/diced into smaller portions corresponding to individual components/structures (when numerous components/structures are processed on a single dielectric layer). The cut/diced portions (or the entirety of the laminated structure in some embodiments) are cofire. The temperature profile employed during cofiring depends on a number of factors including, but not limited to, whether low temperature cofire ceramic (LTCC) materials or high temperature cofire ceramic (HTCC) materials are employed in the cofire structure.

Dielectric material can then be provided. In one embodiment, the dielectric material can be a tape generated by a tape casting process, for example. Tape casting is a process employed to produce thin tapes (e.g., ceramic tapes) from ceramic slurry. One example process includes placing ceramic slurry in a chamber having a small gap controlled by a doctor blade. A polymer tape is then passed under the gap and slurry forms on the surface at the thickness dictated by the doctor blade gap. The slurry and tape pass through the oven, evaporating the liquid and forming a solid ceramic tape on a polymer backing. The tape then exits the oven and is wound onto a spool structure. While the above embodiment describes tape casting for generating the dielectric material, in other embodiments, the dielectric layer can be provided via a pre-formed ceramic green sheet.

In embodiments in which the CCS will be located inside of a hermetically sealed housing, the dielectric layer need not be composed of biocompatible and biostable ceramic material. However, in embodiments in which the CCS will not be located in a hermetically sealed housing (e.g., if the CCS will be located in a plastic header), the dielectric layer can be composed of biocompatible and biostable ceramic material. Exemplary biostable and/or biocompatible dielectric material can include, but is not limited to, oxides of aluminum, zirconium, silicon, niobium, tantalum, and mixtures of their oxides.

In other embodiments, dielectric layers that will be external surfaces to the CCS can be coated with material that is biostable and biocompatible while other dielectric layers can be non-biostable and non-biocompatible. Coating can be performed by a number of different methods including, but not limited to, chemical vapor deposition, physical vapor deposition, electron-beam evaporation sputtering or plating.

Dielectric layers can be composed of LTCC or HTCC material. LTCC material generally has a sintering temperature of less than about 1000° Celsius. By way of example, but not limitation, LTCC material can be glass bonded ceramics of composition that suitably densifies in the 850°-1000° Celsius range. In some embodiments, LTCC material can have a sintering temperature of between about 850° and 900° Celsius. HTCC material generally has a sintering temperature greater than about 1000° Celsius (and typically approximately 1600° Celsius). In some embodiments, HTCC material can have a sintering temperature of between about 1100° and 2100° Celsius. By way of example, but not limitation, HTCC material can be alumina and/or aluminum nitride.

In embodiments employing tape casting, the tape is cut to dimensions/shape suitable for the desired cofire structure/component. The result is a dielectric layer that can be processed in preparation for cofiring. In various embodiments, numerous dielectric layers can be processed in parallel or in series according to the above-described steps. The numerous layers can then be cofired together, simultaneously.

In some embodiments, one or more apertures are provided in the dielectric layer. For example, the apertures can be apertures for vias between layers of dielectric that will form the CCS and/or hollow cavity. In some embodiments, the region of the dielectric layers that will have the hollow region post-cofiring can be roughly formed prior to cofiring. For example, the hollow region can be roughed out by removing material in the region prior to cofiring. In some instances, however, the hollow cavity may be formed in the CCS after cofiring.

A support structure can be provided in the hollow cavity in some embodiments to reduce the likelihood of portions of the dielectric layer sinking into the cavity during cofiring. After cofiring, machining using standard ceramic shaping and polishing methods can be employed to smooth interior walls of the cavity and/or to achieve the final desired dimensions of the hollow cavity. In some embodiments, apertures for vias are formed; however, the hollow cavity is formed after cofiring. In either approach, numerous approaches can be employed for providing the apertures in the dielectric layer including, but not limited to, mechanical punching, laser drilling or mechanical drilling.

Further, in some embodiments, molds can be employed to form dielectric layers have apertures and/or cavities of desired shape and size. In some embodiments, the shape of the periphery of the dielectric layer can be substantially the same or similar to the shape of the hollow cavity. In other embodiments, the shape of the periphery of the dielectric layer can be different from the shape of the hollow cavity. By way of example, but not limitation, shapes of the periphery and/or the hollow cavity can include, but are not limited to, ovals, concentric circles, squares, rectangles, rounded squares or irregular shapes.

Additionally, in some embodiments, one or more of the dielectric layers can be formed without a hollow cavity. Such dielectric layers can be provided as layers that will be external surfaces of the CCS (after collating, laminating and cofiring) in embodiments in which the CCS includes one or more closed ends. As such, dielectric layers intended for the interior surfaces of CCS can have a hollow region while dielectric layers intended for one or more of the exterior surfaces of CCS can be formed without any hollow region. Accordingly, in different embodiments, CCSs can be formed with one closed end, two closed ends (and a hollow interior) or two open ends.

The apertures for the vias can be provided at positions corresponding to desired locations of vias that will provide electrical connection between the layers of dielectric material after cofiring is completed. The above-described method illustrates a method for an exemplary antenna that is substantially helical-shaped. As such, aperture position corresponds to expected locations of conductive material that will form the antenna after cofiring. Other arrangements of aperture position are possible in accordance with the desired antenna configuration (e.g., substantially serpentine-shaped antenna), for example.

Next, locations for post-firing vias are created by filling apertures with conductive paste. In various embodiments, conductive paste can be deposited to create a conductive path between the different layers of dielectric material after cofiring. Specifically, the vias can form electrical interconnections along a z-axis of a cofire stack of numerous dielectric layers.

The vias can be filled with the conductive paste using vacuum assisted screen printing in some embodiments.

In embodiments in which the CCS will be located inside of a hermetically sealed housing, the conductive paste can be conductive non-biocompatible and non-biostable material. Exemplary materials that are not biostable and not biocompatible that can be employed include, but are not limited to, copper, molybdenum and tungsten.

However, in embodiments in which the CCS will not be located in a hermetically sealed housing (e.g., if CCS 400 will be located in a plastic header), conductive paste can be or include one or more conductive materials that are biostable and biocompatible. Conductive materials that are biostable can include, but are not limited to, platinum, palladium, platinum, iridium, silver-palladium, platinum-iridium, and/or mixtures including such conductive materials.

The determination of which biostable conductor materials to use can be a function of whether an LTCC or HTCC system will be employed for cofiring. For example, for LTCC systems, metals with lower melting temperatures can be employed. For HTCC systems, metals with higher melting temperatures can be employed (e.g., platinum, iridium, palladium and their mixtures).

Via hermeticity can be very advantageous towards long-term implantation of the CCS. Hermeticity can be achieved upon cofiring conductive paste having particular characteristics. For example, conductive pastes that include platinum and alumina combinations can result in hermetic vias upon cofiring (when the conductive material of the antenna includes or is alumina). In some embodiments, this conductive paste is combination of platinum (e.g., platinum powder) and an alumina (e.g., aluminum oxide, corundum) additive. For example, in some embodiments, the conductive paste can include at least 70% alumina, about 92% alumina or about 96% alumina. Some examples of via composition and processes for forming vias are described in U.S. Patent Publication No. 2013/0032378 (Morioka, et al.), entitled "Hermetic Feedthrough" and U.S. Patent Publication No. 2013/0032391 (Morioka et al.), entitled "Feedthrough Configured For Interconnect," both of which are incorporated by reference herein in their entirety.

In some embodiments, the platinum power can be composed of a first platinum powder that has a median particle size between about 3 um and about 10 um (e.g., $d_{50}$ median particle size), a second platinum powder having a median particle size between about 5 um and about 20 um or a combination of the first and second platinum powders. Use of particles of different size for the materials of the conductive paste, including the additives, can change the thermal expansion response and/or sintering kinetics and properties (e.g., sintering shrinkage, shrinking profile) of the conductive paste.

As noted above, the incorporation of the alumina additive in the platinum powder can result in a cofire hermetic bond between the via and the antenna in embodiments in which the antenna is composed of alumina. In particular, the alumina in the platinum powder can bond with the alumina from which the antenna is composed along the boundary between the via and the antenna. Such bond at the boundary can increase the likelihood of achieving a hermetic seal (relative to embodiments that utilize conductive paste that does not include alumina). As such, incorporating alumina into the conductive paste (when the conductive material from which the antenna is composed is or also includes alumina) can result in a hermetic seal between the via and the antenna. As such, in some cases, body fluids can be prevented from passing through the via and damaging components of CCS 400 and/or allowing leakage of materials integrated in the CCS to the patient. Long-term implantation can then be facilitated.

Next, screen printing of various materials for the antenna and/or components to be cofire-integrated can be provided on the dielectric layer. For example, metal traces for the antenna can be provided overlapping at least some portion of the conductive paste with which the vias are filled to facilitate electrical conductivity across numerous layers of the CCS after cofiring.

As another example, as shown, material from a component formed post-cofiring can also be provided at least, in part, in connection with the dielectric layer. For example, in some embodiments, a portion of the material for the component can be screen printed on the dielectric layer and a second portion of the material can be provided in the hollow region of the dielectric layer. In this regard, a support structure (not shown) can be provided on an underside of the material from which the component is formed. As such, the material can be stabilized by the support structure through the lamination step in some embodiments, and through the cofiring step, in other embodiments.

Screen printing can be employed in some embodiments to perform the metal deposition. Screen printing is a thick film technology that includes pushing ink through a patterned screen or stencil having cutout regions coinciding with a desired design and/or location of materials on a surface. The material printed on the layer can be cured at high temperature (e.g., 50° Celsius to 200° Celsius) to dry and fix the material temporarily in position on the layer. In some embodiments, the material can be cured by exposure to ultraviolet (UV) light.

The conductive material can be screen printed in a configuration suitable to the design of the eventual antenna. By way of example, but not limitation, the metal traces of the antenna can be formed in the x-y plane of the dielectric layer. The metal traces can be printed on the same dielectric layers with the vias.

The conductive material can be provided in connection with the conductive paste to provide electrical conductivity between the antenna and the via thereby facilitating conductivity across layers of the CCS. While screen printing is described, in other embodiments, different approaches for material deposition can be employed. Deposition approaches can include, but are not limited to, plating, spraying or the like.

Portions of conductive material can be located at different positions on the layer of dielectric material based on the desired configuration of the antenna to be formed from the conductive material. By way of example, but not limitation, the conductive material can be placed in a first set of positions on a dielectric layer if a substantially serpentine-shaped antenna is desired and/or placed in a second set of positions on a dielectric layer if a substantially helical-shaped antenna is desired.

In some embodiments, the two layers of dielectric material that will be closest to an external surface of the CCS after cofiring can be provided without conductive material. As such, there will be at least two layers of dielectric between metal and the surface of the CCS that will contact bodily tissue.

In embodiments in which the antenna will not be encased in a hermetically sealed housing, the conductive material can be biostable and/or biocompatible. Exemplary biostable and/or biocompatible dielectric material can include, but are not limited to those described supra for conductive paste of the via.

In embodiments in which the antenna will be encased in a hermetically sealed housing, and therefore not likely to be exposed to bodily fluid and/or gases, the conductive material need not be biostable and biocompatible. Exemplary biostable and/or biocompatible dielectric material can include, but are not limited to those described supra for conductive paste of the via.

While the above step describes screen printing of conductive material for the antenna, in various other embodiments, any number of different components having elements that can withstand cofiring temperature can be provided on or between the dielectric layers to form components in a wall of the CCS and/or in the hollow cavity of the CCS upon cofiring. For example, material for any type of passive electrical component, active electrical component or combination thereof can be deposited onto one or more dielectric layers. As another example, material for an integrated circuit and/or passive network can be deposited onto one or more dielectric layers. In some embodiments, the material for the components can be deposited entirely or partly in the hollow region. In some embodiments, the component within the hollow cavity is not electrically or mechanically connected to the wall that forms the periphery of the hollow cavity.

Upon cofiring, the component and the antenna can each be cofire-integrated, at least in part, into the wall of the CCS. As such, greater functionality can be integrated into the CCS as desired thereby reducing the footprint of the overall IMD.

The numerous layers of dielectric are collated and laminated to form a laminated structure. Lamination is performed at high heat with pressure applied to the stack of layers to cause the stack of layers to adhere to one another. Accordingly, geometric registration can be maintained between the dielectric layers (and vias). Lamination can also cause a high densification of the material provided on the layers, which can result in more effective sintering during cofiring. In some embodiments, lamination includes applying 3000 pressure per square inch (psi) at 70-80° Celsius for approximately 10 minutes. In various embodiments, however, the temperature and time during which the collated stack is heated can vary.

Next, the laminated structure is cofired and the CCS results. For example, with reference to FIG. 3, the CCS can be CCS 302 while, with reference to FIG. 4A, the CCS can be CCS 400. Cofiring refers to the process of simultaneously sintering the ceramic and all materials deposited on the ceramic to densify the laminated structure. The temperature at which the laminated structure is cofired depends on whether the materials of which the dielectric layer is composed are LTCC or HTCC materials. For example, for LTCC materials, cofiring at between 850° Celsius and 900° Celsius can be employed. For HTCC materials, cofiring at 1600° Celsius can be employed.

Although not shown, in embodiments in which numerous structures are being fabricated on each layer, prior to cofiring, the laminated structure can be cut/diced into numerous portions corresponding to the different locations of the structures being fabricated. For example, the laminated structure can be cut into four different portions corresponding to the locations of four CCSs being fabricated.

Conventional wafer dicing methods can be employed in some embodiments. Methods can include, but are not limited to, scribing and breaking, mechanical sawing or laser cutting.

The above description illustrates one example of a method of fabricating a CCS having a cofire-integrated antenna. Other embodiments can differ in any number of ways including, but not limited to, number of layers of dielectric material collated and laminated, the configuration of the conductive material, the type of materials employed, the locations of the vias, the components cofire in the CCS in addition to the antenna or the like. In some embodiments, dielectric material for forming capacitive interconnections can be provided on the conductive material prior to cofiring to form capacitive interconnections between portions of the antenna to provide electrical connectivity (in lieu of forming vias between portions of the antenna).

Cofire ceramic technology can advantageously enable efficient antenna designs for IMDs because complex antenna designs can be facilitated and high dielectric properties of the CCS resulting from the cofire process can better match body tissue inside the human body. Further, one or more embodiments described herein can facilitate significant RF performance, and thereby enable satisfactory RF signal ranges.

In the embodiment shown, tape casting is performed as a first step. However, in embodiments in which a pre-formed ceramic green sheet, or green tape, is used, the process can include steps shown and described above. Further, other CCSs described herein can be fabricated according to the approach described above.

Figure 15:
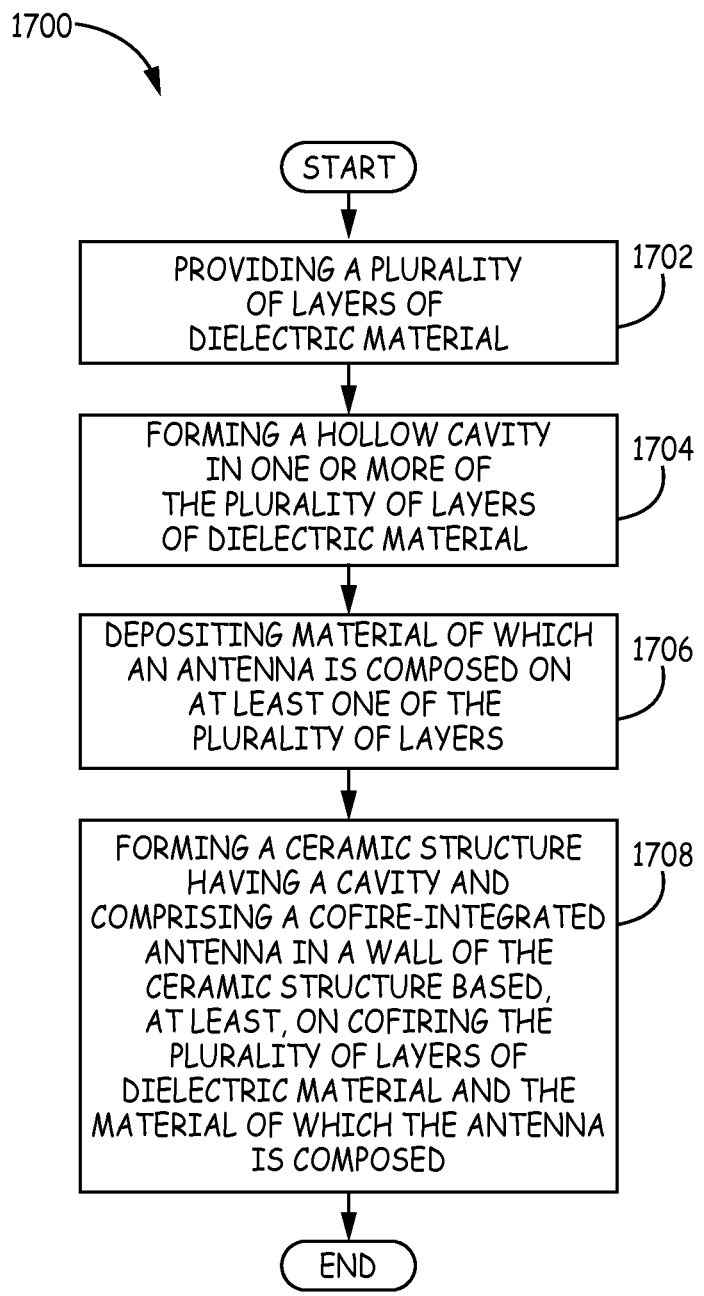
FIGS. 15, 16 and 17 illustrate flow charts of exemplary non-limiting methods of fabricating IMDs in accordance with embodiments described herein.
Figure 16:
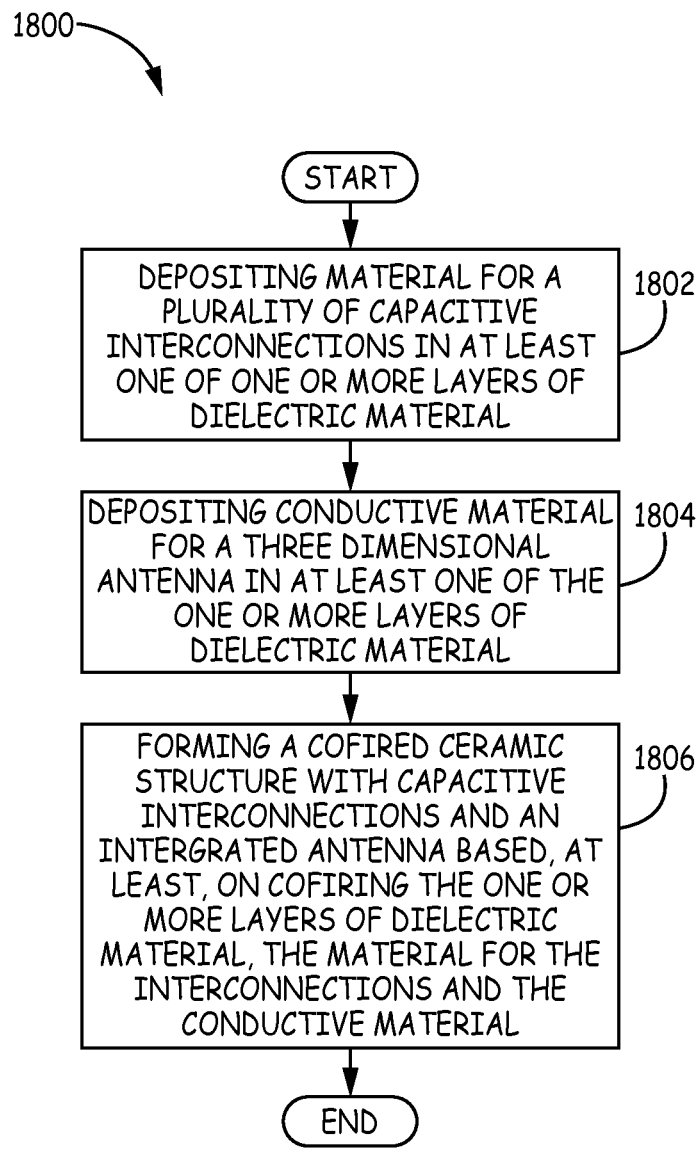
Figure 17:
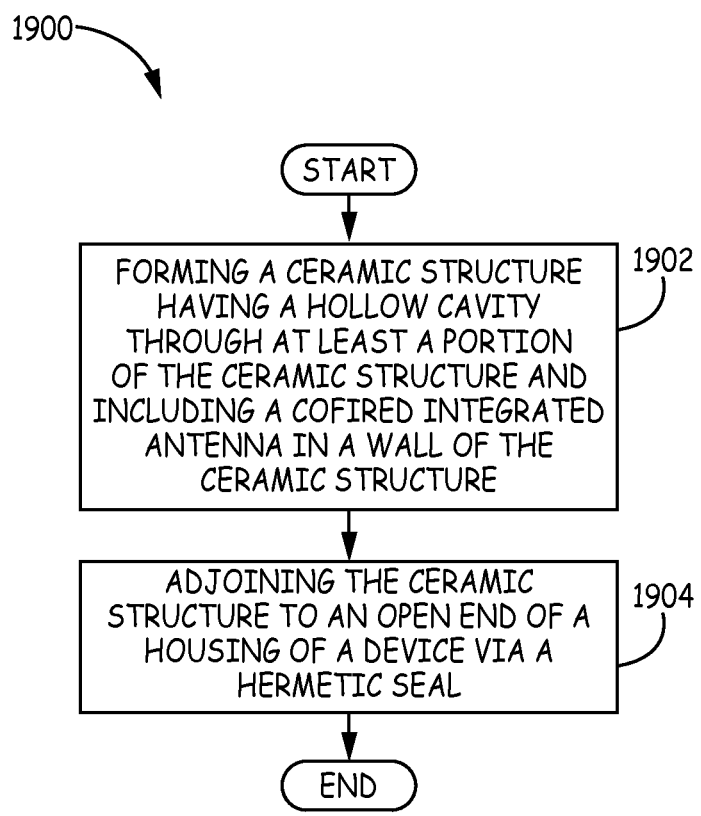

FIGS. 15, 16 and 17 illustrate flow charts of methods of fabricating IMDs in accordance with embodiments described herein. Turning now to FIG. 15, at 1702, method 1700 can include providing a plurality of layers of dielectric material. At 1704, method 1700 can include forming a hollow cavity in one or more of the plurality of layers of dielectric material. In other instances, at least a portion of the plurality of dielectric layers may come with the hollow cavity already formed in the layers.

At 1706, method 1700 can include depositing material of which an antenna is composed on at least one of the plurality of layers. The configuration in which the material is deposited can be dictated by the desired configuration of the three-dimensional antenna after cofiring.

Although not shown, in some embodiments, two portions of conductive material can be deposited on a dielectric layer substantially parallel to one another to form substantially parallel capacitive interconnections. While the interconnections are substantially parallel in this embodiment, in other embodiments, the capacitive interconnections need not be substantially parallel yet can be positioned relative to one another to cause a substantially capacitive interconnection between one another. Numerous capacitive interconnections can be provided across different dielectric layers provide capacitive interconnections in at least one of the plurality of layers of dielectric material. Further, in some embodiments, materials for components that can withstand cofire sintering temperatures can be provided in the hollow cavity.

At 1708, method 1700 can include forming a ceramic structure having a cavity and comprising a cofire-integrated antenna in a wall of the ceramic structure based, at least, on cofiring the plurality of layers of dielectric material and the material of which the antenna is composed.

Turning now to FIG. 16, at 1802, method 1800 can include depositing material for a plurality of capacitive interconnections in at least one of one or more layers of dielectric material. At 1804, method 1800 can include depositing material for a three dimensional antenna in at least one of the one or more layers of dielectric material. At 1806, method 1800 can include forming a cofired ceramic structure with capacitive interconnections and an integrated antenna based, at least, on cofiring the one or more layers of dielectric material, the material for the capacitive interconnections and the conductive material.

Turning now to FIG. 17, at 1902, method 1900 can include forming a ceramic structure having a hollow cavity through at least a portion of the ceramic structure and including a cofired integrated antenna in a wall of the ceramic structure. At 1904, method 1900 can include adjoining the ceramic structure to an open end of a housing. The ceramic structure can be adjoined to the housing via a hermetic seal in some embodiments. Further, one or more components can be deposited in the housing prior to adjoining the housing to the ceramic structure.

Some of the embodiments, such as those described with reference to medical telemetry system 100 of FIG. 1, medical telemetry system 100' of FIG. 2 or medical telemetry system 1500 of FIG. 13 can be practiced in computing environments. In these environments, certain tasks can be performed by remote processing devices that are linked through a communications network. Also, some of the embodiments include computing devices (e.g., external device 104) having computer-executable instructions that can be executed by processors to perform one or more different functions. Those skilled in the art will recognize that the embodiments can be also implemented in combination with hardware and/or software.

Computing devices typically include a variety of media, which can include computer-readable storage media and/or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data or unstructured data. Tangible and/or non-transitory computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD) or other optical disk storage, magnetic cassettes, magnetic tape, magnetic disk storage, other magnetic storage devices and/or other media that can be used to store desired information. Computer-readable storage media can be accessed by one or more local or remote computing devices (e.g., via access requests, queries or other data retrieval protocols) for a variety of operations with respect to the information stored by the medium.

In this regard, the term "tangible" herein as applied to storage, memory or computer-readable media, is to be understood to exclude only propagating intangible signals per se as a modifier and does not relinquish coverage of all standard storage, memory or computer-readable media that are not only propagating intangible signals per se. In this regard, the term "non-transitory" herein as applied to storage, memory or computer-readable media, is to be understood to exclude only propagating transitory signals per se as a modifier and does not relinquish coverage of all standard storage, memory or computer-readable media that are not only propagating transitory signals per se.

Communications media typically embody computer-readable instructions, data structures, program modules or other structured or unstructured data in a data signal such as a modulated data signal, e.g., a channel wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

What has been described above includes mere examples of various embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the detailed description and the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An implantable medical device (IMD) comprising:
 a ceramic structure having at least one wall defining a hollow cavity, wherein the ceramic structure includes a first end and a second end distal from the first end, the first and second ends being open to provide access to the hollow cavity;
 an antenna cofire-integrated into the at least one wall of the ceramic structure; and
 a housing adjoined to the ceramic structure.

2. The IMD of claim 1, further comprising a component located within the hollow cavity of the ceramic structure.

3. The IMD of claim 2, wherein the component comprises at least one of a component of an integrated circuit or a component of a passive network.

4. The IMD of claim 2, wherein the component is configured to perform one or more electrical functions.

5. The IMD of claim 1, further comprising a component cofire-integrated into the wall of the ceramic structure.

6. The IMD of claim 1, wherein the ceramic structure includes a plurality of dielectric layers and the antenna includes a plurality of conductive traces each of which is on a different one of the dielectric layers, further wherein each of the dielectric layers including a conductive trace is separated by one or more dielectric layers.

7. The IMD of claim 6, wherein each of the plurality of conductive traces of the antenna are interconnected with a plurality of conductive vias that extend through the one or more dielectric layers separating the conductive traces.

8. The IMD of claim 6, further comprising at least one pair of capacitive interconnections that interconnect conductive traces on different ones of the dielectric layers.

9. The IMD of claim 8, wherein the capacitive interconnections are cofire-integrated into the ceramic structure.

10. The method of claim 6, wherein the plurality of conductive traces are interconnected to form an antenna that is at least one of substantially serpentine-shaped, substantially helical-shaped, substantially spiral-shaped, substantially fractal-shaped or meandering.

11. The IMD of claim 1, wherein the antenna is configured to communicate a radio frequency signal.

12. The IMD of claim 1, wherein the ceramic structure comprises a high temperature cofire ceramic material having a sintering temperature greater than about 1000° Celsius.

13. The IMD of claim 1, wherein the ceramic structure comprises material or a mixture composed of at least one of platinum, palladium, platinum, iridium, silver-palladium, platinum-iridium, niobium or tantalum.

14. The IMD of claim 1, wherein the housing includes a first housing component adjoined to the first end of the ceramic structure and a second housing component adjoined to the second end of the ceramic structure.

15. The IMD of claim 1, wherein the housing is adjoined to the ceramic structure and the first and second ends to form a hermetic seal.

16. The IMD of claim 1, wherein the IMD further comprises:
   a power source within the housing; and
   electrical circuitry within the housing.

17. The IMD of claim 16, wherein the IMD comprises at least one of an implantable therapy lead, an implantable sensor, an implantable monitor, an implantable cardioverter defibrillator, an implantable neurostimulator, an implantable physiological monitor or an implantable pulse generator.

18. The IMD of claim 17, further comprising a component cofire-integrated into the wall of the ceramic structure and electrically coupled to the electrical circuitry within the housing.

19. The IMD of claim 18, wherein the component comprises an electrode.

20. The IMD of claim 1, further comprising a metal pad cofire-integrated into an external surface of the ceramic structure to provide an electrical connection between the cofire-integrated antenna and one or more components of the IMD.

21. The IMD of claim 1, further comprising a second antenna cofire-integrated into the at least one wall of the ceramic structure to provide for antenna diversity.

* * * * *